(12) United States Patent
Yacoby et al.

(10) Patent No.: US 11,324,619 B1
(45) Date of Patent: May 10, 2022

(54) ACUTE AND CHRONIC DEVICES FOR MODIFYING FLOW IN BODY LUMENS AND METHODS OF USE THEREOF

(71) Applicant: Nephronyx Ltd., Modiin (IL)

(72) Inventors: Menashe Yacoby, Shoham (IL); Oren Rotman, Holon (IL); Sagy Karavany, Kibbutz Dvir (IL); Tanhum Feld, Moshav Merhavya (IL); Eyal Teichman, Hod-Hasharon (IL)

(73) Assignee: Nephronyx Ltd., Modiin (IL)

( * ) Notice: Subject to any disclaimer, the term of this patent is extended or adjusted under 35 U.S.C. 154(b) by 0 days.

(21) Appl. No.: 17/646,114

(22) Filed: Dec. 27, 2021

Related U.S. Application Data

(63) Continuation of application No. PCT/IB2021/054612, filed on May 26, 2021.
(Continued)

(51) Int. Cl.
*A61F 2/966* (2013.01)
*A61F 2/07* (2013.01)
(Continued)

(52) U.S. Cl.
CPC ............... *A61F 2/966* (2013.01); *A61F 2/07* (2013.01); *A61F 2002/068* (2013.01); *A61F 2002/9528* (2013.01); *A61F 2250/0039* (2013.01)

(58) Field of Classification Search
CPC ...... A61F 2/966; A61F 2/07; A61F 2002/068; A61F 2002/9528; A61F 2250/0039
See application file for complete search history.

(56) References Cited

U.S. PATENT DOCUMENTS 6,120,534 A 9/2000 Ruiz
6,743,196 B2 6/2004 Barbut et al.
(Continued)

FOREIGN PATENT DOCUMENTS

WO WO-0197717 A1 12/2001
WO WO-2005048871 A2 6/2005
(Continued)

OTHER PUBLICATIONS

U.S. Appl. No. 15/995,101, U.S. Appl. No. 10/195,406, filed May 31, 2018, Feb. 5, 2019.
(Continued)

*Primary Examiner* — Kelly J Bekker
*Assistant Examiner* — Andrew P. Restaino
(74) *Attorney, Agent, or Firm* — Eversheds Sutherland (US) LLP; Christopher C. Bolten; Albert K. Heng

(57) ABSTRACT

The acute and chronic devices and methods described herein include a body lumen fluid flow modulator including an upstream flow accelerator and a downstream flow decelerator. The fluid flow modulator preferably includes one or more openings that define a gap/entrainment region that provides a pathway through which additional fluid from a branch lumen(s) is entrained into the fluid stream flowing from the upstream flow accelerator to the downstream flow decelerator. Delivery devices including a sheath and inner assembly also are provided for delivering the flow modulator to the body lumen. The delivery device may maintain the flow modulator in its collapsed, delivery state upon retraction of the sheath for ease of readjustment within the body lumen prior to full deployment of the flow modulator within the body lumen.

28 Claims, 15 Drawing Sheets

Related U.S. Application Data

(60) Provisional application No. 63/031,491, filed on May 28, 2020.

(51) Int. Cl.
    *A61F 2/06*     (2013.01)
    *A61F 2/95*     (2013.01)

(56) References Cited

U.S. PATENT DOCUMENTS

| | | |
|---|---|---|
| 7,048,702 B2 | 5/2006 | Hui |
| 7,384,389 B2 | 6/2008 | Anzellini |
| 9,204,958 B2 | 12/2015 | LaDuca et al. |
| 9,764,113 B2 | 9/2017 | Tuval et al. |
| 10,195,406 B2 | 2/2019 | Karavany et al. |
| 2001/0021872 A1 | 9/2001 | Bailey et al. |
| 2004/0133260 A1 | 7/2004 | Schwartz et al. |
| 2004/0143319 A1 | 7/2004 | Schwartz et al. |
| 2005/0043790 A1 | 2/2005 | Seguin |
| 2005/0222674 A1 | 10/2005 | Paine |
| 2006/0106449 A1 | 5/2006 | Ben Muvhar |
| 2006/0149360 A1 | 7/2006 | Schwammenthal et al. |
| 2007/0185565 A1 | 8/2007 | Schwammenthal et al. |
| 2007/0293808 A1 | 12/2007 | Williams et al. |
| 2009/0270965 A1 | 10/2009 | Sinha et al. |
| 2010/0036307 A1 | 2/2010 | Von Segesser |
| 2010/0063578 A1 | 3/2010 | Ren et al. |
| 2010/0145433 A1 | 6/2010 | Anukhin et al. |
| 2011/0306916 A1 | 12/2011 | Nitzan et al. |
| 2012/0095547 A1 | 4/2012 | Chuter |
| 2012/0165928 A1 | 6/2012 | Nitzan et al. |
| 2013/0338761 A1 | 12/2013 | Plowiecki et al. |
| 2014/0350565 A1 | 11/2014 | Yacoby et al. |
| 2014/0350658 A1 | 11/2014 | Benary et al. |
| 2015/0039020 A1 | 2/2015 | Cragg et al. |
| 2015/0238315 A1 | 8/2015 | Rabito et al. |
| 2016/0128983 A1 | 5/2016 | Djonov et al. |
| 2017/0112986 A1 | 4/2017 | Heuring et al. |
| 2017/0128705 A1 | 5/2017 | Forcucci et al. |
| 2017/0156845 A1 | 6/2017 | Florescu |
| 2018/0014829 A1 | 1/2018 | Tal et al. |
| 2018/0280667 A1 | 10/2018 | Keren |
| 2019/0167878 A1 | 6/2019 | Rowe |
| 2019/0239998 A1* | 8/2019 | Tuval ........................ A61F 2/06 |
| 2019/0298509 A1 | 10/2019 | Sohn |
| 2021/0236727 A1 | 8/2021 | Levin et al. |
| 2021/0244381 A1 | 8/2021 | Sweeney et al. |

FOREIGN PATENT DOCUMENTS

| | | |
|---|---|---|
| WO | WO-2013183060 A2 | 12/2013 |
| WO | WO-2014141284 A2 | 9/2014 |
| WO | WO-2015177793 A2 | 11/2015 |
| WO | WO-2016128983 A1 | 8/2016 |
| WO | WO-2016185473 A1 | 11/2016 |
| WO | WO-2018029688 A1 | 2/2018 |
| WO | WO-2018061002 A1 | 4/2018 |
| WO | WO-2018220589 A1 | 12/2018 |
| WO | WO-2019097424 A2 | 5/2019 |
| WO | WO-2019186538 A1 | 10/2019 |
| WO | WO-2020109979 A1 | 6/2020 |

OTHER PUBLICATIONS

U.S. Appl. No. 16/617,479, filed Nov. 26, 2019.
U.S. Appl. No. 17/296,199, filed May 21, 2021.
International Search Report & Written Opinion dated Feb. 13, 2020 in Int'l. PCT Patent Appl. Serial No. PCT/IB2019/060142 (0510). 14 pages.
International Search Report & Written Opinion dated Aug. 18, 2021 in Int'l. PCT Patent Appl. Serial No. PCT/IB2021/054612 (0610). 11 pages.
Int'l Search Report & Written Opinion dated Sep. 17, 2018 in Int'l. PCT Patent Appl. Serial No. PCT/IB2018/053925 (0410). 14 pages.

* cited by examiner

ACUTE AND CHRONIC DEVICES FOR MODIFYING FLOW IN BODY LUMENS AND METHODS OF USE THEREOF

CROSS-REFERENCE TO RELATED APPLICATIONS

This application is a continuation of PCT International Application No. PCT/IB2021/54612, filed May 26, 2021, which claims the benefit of priority of U.S. Provisional Application Ser. No. 63/031,491, filed May 28, 2020, the entire contents of each of which are incorporated herein by reference. This application is related to PCT International Application No. PCT/IB2019/060142, filed Nov. 25, 2019, published as WO 2020/109979, which claims the benefit of priority of U.S. Provisional Application Ser. No. 62/873,755, filed Jul. 12, 2019, and U.S. Provisional Application Ser. No. 62/771,559, filed Nov. 26, 2018, the entire contents of each of which are incorporated herein by reference. This application is related to U.S. patent application Ser. No. 15/995,101, filed May 31, 2018, now U.S. Pat. No. 10,195,406, and PCT International Application No. PCT/IB2018/053925, filed May 31, 2018, published as WO 2018/220589, each of which claims the benefit of priority of U.S. Provisional Application Ser. No. 62/537,067, filed Jul. 26, 2017, and U.S. Provisional Application Ser. No. 62/514,020, filed Jun. 2, 2017, the entire contents of each of which are incorporated herein by reference.

FIELD OF THE INVENTION

The present invention relates generally to acute and chronic devices and methods for altering flow in body lumens, such as devices and methods for creating pressure differences and/or entrainment of fluid at lumens that branch off from other lumens for enhancing or modifying fluid flow to treat different disorders or diseases.

BACKGROUND OF THE INVENTION

Heart failure is the physiological state in which cardiac output is insufficient to meet the needs of the body and the lungs. Patients suffering from any of a number of forms of heart failure are prone to increased fluid in the body. Congestive heart failure (CHF) occurs when cardiac output is relatively low and the body becomes congested with fluid. There are many possible underlying causes of CHF, including myocardial infarction, coronary artery disease, valvular disease, and myocarditis. Chronic heart failure is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the heart's contractions become weakened, and the heart failure worsens. Another compensatory mechanism is vasoconstriction of the arterial system. This mechanism, like salt and water retention, raises the blood pressure to help maintain adequate perfusion.

Glomerular filtration rate (GFR), the rate at which the kidney filters blood, is commonly used to quantify kidney function and, consequently, the extent of kidney disease in a patient. Individuals with normal kidney function exhibit a GFR of at least 90 mL/min with no evidence of kidney damage. The progression of kidney disease is indicated by declining GFR, wherein a GFR below 15 mL/min generally indicates that the patient has end stage renal disease (ESRD), which is the complete failure of the kidney to remove wastes or concentrate urine.

In addition to increases in total body salt and water, it has also been found that altered capacitance of the splanchnic venous vessels change the blood volume distribution. Decreased venous capacitance can lead to shifts of fluid from the venous reservoir into the effective circulatory volume/splanchnic circulation, thus increasing filling pressures. This could result in clinical heart congestion.

Cardiovascular problems, such as but not limited to, inadequate blood flow or chronic hypertension, may lead to fluid retention in the kidneys, chronic kidney disease, lowered GFR, renal failure or even ESRD. For example, hypertension is considered the second most prevalent cause for kidney failure (after diabetes). It has been estimated that hypertension causes nephrotic damage and lowers GFR.

Transjugular intrahepatic portosystemic shunt (TIPS or TIPSS) is an artificial channel within the liver that establishes communication between the inflow portal vein and the outflow hepatic vein. Generally, under imaging guidance, a small metal stent is placed to keep the channel open and allow the channel to bring blood draining from the bowel back to the heart while avoiding the liver. TIPS may be used to treat conditions such as portal hypertension (often due to liver cirrhosis) which frequently leads to intestinal bleeding, life-threatening esophageal bleeding (esophageal varices), and the buildup of fluid within the abdomen (ascites), and has shown promise for treating hepatorenal syndrome. A drawback of TIPS is that blood meant to be filtered by the liver bypasses the liver via the artificial channel, which may cause complications.

Therefore, it would be desirable to provide acute and/or chronic apparatus and methods to improve blood flow to prevent disease, improve body functionality, and/or treat conditions that would benefit from modified body fluid flow. For example, it would be desirable to treat heart failure, treat hypertension, prevent kidney disease, improve kidney functionality, restore normal values of splanchnic circulation, improve liver functionality, enhance or replace TIPS, and/or prevent blood clots from flowing through vasculature to sensitive portions of the body, such as the brain, in order to prevent strokes.

It would further be desirable to provide delivery systems for delivering a flow modulator device that permits readjustment of the device within a body lumen prior to fully deploying the device within the body lumen.

SUMMARY OF THE INVENTION

The present invention seeks to provide acute and chronic devices and methods for altering flow in body lumens. For example, devices and methods are provided for creating pressure differences and/or fluid entrainment at lumens that branch off from other lumens for enhancing or modifying fluid flow to treat different disorders or diseases. For positioning, the device may be acutely or chronically implanted within the body lumen.

The devices and methods of the present invention have many applications. For example, the device may be used to reduce pressure and improve flow, thereby improving flow in stenotic body lumens. It also may be used in the aortic arch to reduce peak systolic pressure in the brain or divert emboli to other portions of the body (e.g., the legs) and thereby reduce the risk of stroke. The device further may be installed in a bifurcation (e.g., in the brachiocephalic vessels) to reduce peak pressure gradients or to divert emboli with very little energy loss.

The devices and methods of the present invention have particular application in treating blood flow to and from the kidneys. In accordance with one embodiment, the device is configured to be installed near one of the renal arteries or in the inferior vena cava near the branch off to the renal veins or in one of the renal veins. When installed in the inferior vena cava or in the renal vein, the device can create (due to the Bernoulli effect or other factors) a region in the inferior vena cava or in the renal vein which has increased blood velocity and reduced pressure. In this manner, blood may be drawn from the kidneys to the renal veins and then to the inferior vena cava, thereby improving kidney functionality and reducing necrotic damage to the kidneys.

When installed in or near the renal vein, the devices of the present invention may improve renal function by improving net filtration pressure, which is glomerular capillary blood pressure−(plasma-colloid osmotic pressure+Bowman's capsule hydrostatic pressure), e.g., 55 mm Hg−(30 mm Hg+15 mm Hg)=10 mm Hg. The devices and methods of the present invention thus provide an improvement over existing therapies, such as diuretics (although the invention can be used in addition to diuretics), angiotensin-converting enzyme inhibitors (ACEIs), and angiotensin receptor blockers (ARBs), which can have deleterious effects on kidney function. When used in conjunction with current modes of treatment such as diuretics, the devices and methods of the present invention are expected to improve the response for diuretics and reduce the dosage needed to obtain therapeutic benefit of such previously known therapies, without the disadvantages of these existing therapies.

The devices and methods of the present invention may be used to divert flow from the kidneys to the inferior vena cava with little energy loss. For example, with a small energy loss due to pressure drop and other fluid factors, a significantly greater increase in blood flow may be achieved. This diversion of flow from the kidneys with little energy loss to increase blood flow is expected to treat conditions such as heart failure and/or hypertension.

It is noted that there is a significant difference between use of an upstream nozzle with no downstream flow decelerator, such as a diffuser. If only an upstream nozzle is placed in the flow path, there is significant energy loss downstream of the nozzle due to the sudden expansion of flow. However, by using a downstream flow decelerator, such as a diffuser, the energy loss is significantly reduced. This leads to another advantage: since the energy loss is significantly reduced, the additional flow that flows into the gap is efficiently added to the flow from the upstream flow accelerator.

In addition, the present invention is expected to provide optimal structure for an upstream flow accelerator when used together with a downstream flow decelerator. For example, the distance between the outlet of the upstream flow accelerator and the inlet of the downstream flow decelerator should be less than a predetermined length to reduce pressure at the gap between the outlet and the inlet.

When installed in the renal artery, the device can reduce pressure applied to the kidneys. Without being limited by any theory, high blood pressure can cause damage to the blood vessels and filters in the kidney, making removal of waste from the body difficult. By reducing the pressure in the renal artery, the filtration rate improves. Although there may be a reduction in the perfusion pressure, the filtration rate will increase because the overall kidney function is more efficient.

It is noted that the fluid flow modulator of the present invention may modulate fluid flow without any input from an external energy source, such as a fan, motor, and the like and without any moving parts. The structure of the device of the invention transfers energy from one lumen flow to another different lumen flow with minimal flow energy losses.

In accordance with one aspect of the present invention, a flow modulator device is provided for altering fluid flow through a body lumen coupled to a branch lumen. The flow modulator device may include an upstream component that is transitionable between a collapsed delivery state and an expanded deployed state. The upstream component has an inlet, an outlet, and a cross-sectional flow area that converges from the inlet towards the outlet in the expanded deployed state. In addition, the upstream component may include a retrieval portion for facilitating retrieval of the flow modulator. For example, the retrieval portion may include a constricted section at an upstream end of the flow modulator, such that the retrieval portion converges from the inlet towards the upstream end in the expanded deployed state. The retrieval portion may include a hook at the constricted section at the upstream end of the flow modulator. For example, the retrieval portion may include one or more eyelets at the upstream end that meet together at the hook. Accordingly, the hook may be pulled to collapse the upstream component. Moreover, the retrieval portion may be coupled to a retrieval device to permit retrieval of the flow modulator. In accordance with one aspect of the present invention, the retrieval portion is configured to remain coupled to the retrieval device for an acute treatment. Additionally, the retrieval portion may be an uncoated portion of a frame forming the fluid modulator.

The flow modulator device further may include a downstream component transitionable between a collapsed delivery state and an expanded deployed state. The downstream component has an entry, an exit, and a cross-sectional flow area that diverges from the entry towards the exit in the expanded deployed state. In addition, the downstream component may include a plurality of anchors radially spaced around a downstream end of the downstream component. The plurality of anchors may be coupled to a delivery device to maintain the downstream component in the collapsed delivery state upon exposure to the body lumen from a sheath of the delivery device. The plurality of anchors may be disengaged from the delivery device to transition the downstream component from the collapsed delivery state and the expanded deployed state.

The flow modulator device further may include an entrainment region between the inlet of the upstream component and the exit of the downstream component. The entrainment region may be integrally formed with the downstream component. The entrainment region may include one or more openings. For example, the one or more openings may include a plurality of openings radially spaced around the entrainment region, e.g., longitudinally extending slots in the flow modulator. Accordingly, the flow modulator may be positioned within the body lumen to accelerate a fluid stream passing through the upstream component towards the downstream component to generate a low pressure region in the vicinity of the entrainment region that entrains additional fluid into the fluid stream via the one or more openings as the fluid stream passes into the downstream component.

The upstream component and the downstream component may be formed from a single frame defining a plurality of cells. The upstream component and the downstream component may be at least partially coated with a biocompatible material, thereby exposing the one or more openings and defining the inlet. The downstream component may have a first diverging portion and a second diverging portion downstream from the first diverging portion, and the second diverging portion's average angle of divergence may be greater than the first diverging portion's average angle of divergence. Additionally, the upstream component may form a nozzle that accelerates the fluid stream passing through the upstream component and the downstream component may form a diffuser that decelerates the fluid stream having the entrained additional fluid passing through the downstream component. The diameter at the entry of the downstream component is preferably larger than the diameter at the outlet of the upstream component, and thus, the cross-sectional flow area at the outlet of the upstream component is less than the cross-sectional flow area at the entry of the downstream component.

In accordance with one aspect of the present invention, an expandable core may be positioned within the flow modulator. The expandable core may be fluid impermeable such that fluid flowing through the flow modulator flows around the expandable core. The expandable core may be at least partially disposed adjacent to the one or more openings of the fluid modulator. For example, the expandable core may be at least partially disposed in a narrowest point within the flow modulator. In accordance with one aspect of the present invention, the expandable core includes an upstream region and a downstream region. The upstream region includes a first end and a cross-sectional area that increases from the first end towards the downstream region, and the downstream region includes a second end and a cross-sectional area that decreases from the upstream region towards the second end.

In accordance with another aspect of the present invention, a system including the flow modulator device and the delivery device is provided. For example, the system may include a sheath having a lumen sized to hold the flow modulator device therewithin in the collapsed delivery state during delivery, and an inner assembly slidably disposed within the lumen of the sheath to facilitate deployment of the flow modulator device out a distal end of the sheath. The inner assembly may include an end cap that may be removeably coupled to the distal end of the sheath during delivery.

The end cap may include a mount having a plurality of receptacles structured to be releasably engaged with the plurality of anchors of the downstream component, and an outer cover slidably disposed over the plurality of receptacles of the mount, such that, when the outer cover is disposed over the plurality of receptacles and the plurality of anchors, the downstream component of the flow modulator device remains in the collapsed delivery state, and when the outer cover is not disposed over the plurality of receptacles, the plurality of anchors disengages with the plurality of receptacles and the downstream component transitions from the collapsed delivery state to the expanded deployed state. For example, the sheath may be retracted proximally relative to the inner assembly and the flow modulator device in the collapsed delivery state, to expose the flow modulator device out the distal end of the sheath while the plurality of anchors is engaged with the plurality of receptacles such that the downstream component of the flow modulator device remains in the collapsed delivery state, and while the retrieval portion of the upstream component remains coupled to the delivery device. Accordingly, the delivery device and the flow modulator device may be repositioned within the body lumen while the flow modulator is exposed out the distal end of the sheath and in the collapsed delivery state.

In addition, the delivery device further may include the retrieval device that may be coupled to the retrieval portion of the upstream component of the flow modulator device during delivery. Accordingly, the sheath may be moved distally relative to the retrieval device while the retrieval device is coupled to the retrieval portion of the upstream component to transition the flow modulator device from the expanded deployed state to the collapsed delivery state within the lumen of the sheath. The retrieval device may remain coupled to the retrieval portion of the upstream component during an acute treatment. Alternatively, the retrieval device may be decoupled from the retrieval portion of the upstream component to chronically implant the flow modulator device. Moreover, the inner assembly may include an adaptive pattern corresponding to a volume curve of the upstream component and the downstream component in the collapsed delivery state within the sheath. The adaptive pattern may support the flow modulator device in the collapsed delivery state within the sheath to prevent kinking in low volume regions.

In accordance with another aspect of the present invention, a method for altering fluid flow through a body lumen coupled a branch lumen is provided. The method may include positioning the delivery device within the body lumen; retracting the sheath relative to the inner assembly and the flow modulator device to expose the flow modulator device out the distal end of the sheath in the collapsed delivery state while the upstream component remains coupled to the delivery device; disengaging the end cap from the downstream component of the flow modulator device to transition the flow modulator device from the collapsed delivery state to an expanded deployed state within the body lumen; and accelerating a fluid stream passing through an upstream component of the flow modulator device towards the downstream component to generate a low pressure region in the vicinity of an entrainment region of the flow modulator device and to entrain additional fluid into the fluid stream as the fluid stream passes into the downstream component. In the expanded deployed state within the body lumen, the upstream component may be positioned in an inferior vena cava such that an inlet of the upstream component is upstream from a branch off to a renal vein and the downstream component is positioned in the inferior vena cava such that an exit of the downstream component is downstream from the branch off to the renal vein, thereby drawing blood from the renal vein and improving kidney functionality. Alternatively, in the expanded deployed state within the body lumen, the upstream component may be positioned in an inferior vena cava such that an inlet of the upstream component is upstream from a branch off to a hepatic vein and the downstream component is positioned in the inferior vena cava such that an exit of the downstream component is downstream from the branch off to the hepatic vein, thereby drawing blood to the inferior vena cava and improving splanchnic circulation.

The method further may include repositioning the flow modulator device within the body lumen while the flow modulator device is exposed out the distal end of the sheath in the collapsed delivery state prior to disengaging the end cap from the downstream component of the flow modulator device. The method further may include moving the sheath distally relative to the flow modulator device to transition the flow modulator device from the expanded deployed state to the collapsed delivery state within the sheath, and removing the delivery device and the flow modulator device from the body lumen. Additionally or alternatively, the method further may include decoupling the upstream component from the delivery device to chronically implant the flow modulator device within the body lumen, removing the delivery device from the body lumen.

In accordance with yet another aspect of the present invention, another flow modulator device for altering fluid flow through a body lumen coupled to a branch lumen is provided. The flow modulator may include a stent that may be positioned within the body lumen. The stent includes an upstream component having an inlet, an outlet, and a cross-sectional flow area that converges from the inlet towards the outlet, a downstream component having an entry, an exit, and a cross-sectional flow area that diverges from the entry towards the exit, and an entrainment region between the inlet of the upstream component and the exit of the downstream component, the entrainment region comprising one or more openings, e.g., a plurality of openings radially spaced around the entrainment region.

In addition, the flow modulator further includes a core that may be positioned within at least the downstream component of the stent. The core has an upstream region and a downstream region. The upstream region has a first end and a cross-sectional area that increases from the first end towards the downstream region, and the downstream region has a second end and a cross-sectional area that decreases from the upstream region towards the second end. Accordingly, the flow modulator device may accelerate a fluid stream passing through the upstream component towards the downstream component and around the core to generate a low pressure region in the vicinity of the entrainment region that entrains additional fluid into the fluid stream via the one or more openings as the fluid stream passes into the downstream component. The position of the core relative to the stent may be adjustable in vivo. Moreover, the position of the core relative to the stent defines a cross-sectional area of a nozzle formed by the upstream portion and the core. The core may be an expandable member that may be expanded to a predetermined size to define a cross-sectional area of a nozzle formed by the upstream portion and the core. For example, the expandable member may be expanded via inflation.

In accordance with one aspect of the present invention, the core may be coupled to a catheter. Accordingly, a first pressure transducer may be coupled to the catheter upstream of the core and a second pressure transducer may be coupled to the catheter downstream of the core, such that the first and second pressure transducers may measure pressure differential across the flow modulator device.

In accordance with another aspect of the present invention, another flow modulator device for altering fluid flow through a body lumen coupled to a branch lumen is provided. The flow modulator may include a stent that may be positioned within the body lumen. The stent has an inlet, an outlet, and a cross-sectional flow area that converges from the inlet towards the outlet. The flow modulator further may include an expandable core that may be positioned at least partially within the stent to form a circumferential opening between the outlet of the stent and expandable core. The expandable core has an upstream region, a middle region having a uniform cross-sectional area, and a downstream region. The upstream region has a first end and a cross-sectional area that increases from the first end towards the downstream region, and the downstream region has a second end and a cross-sectional area that decreases from the upstream region towards the second end. Accordingly, the flow modulator device may accelerate a fluid stream passing through the stent and around the expandable core through the circumferential opening towards the downstream region to generate a low pressure region in the vicinity of the middle region that entrains additional fluid into the fluid stream as the fluid stream flows over the downstream region.

The expandable core may be selectively expanded to a predetermined size to define the area of the circumferential opening. For example, the expandable core may be expanded via inflation. Moreover, an angle of divergence of the upstream region may be greater than an angle of convergence of the downstream region. In addition, the stent may be formed of a wire frame at least partially coated with a biocompatible material, thereby exposing the inlet and circumferential opening. For example, an upstream end of the stent remains may be coupled to a delivery device for an acute treatment. Additionally, the expandable core may be coupled to a catheter, and a first pressure transducer may be coupled to the catheter upstream of the expandable core and a second pressure transducer may be coupled to the catheter downstream of the expandable core. Accordingly, the first and second pressure transducers may measure pressure differential across the flow modulator device, and the degree of expansion of the expandable core may be based on the pressure measurements.

DETAILED DESCRIPTION OF EMBODIMENTS

Devices and methods for altering flow in body lumens are provided for creating pressure differences and/or to induce fluid entrainment from branch lumens for enhancing or modifying fluid flow to treat different disorders or diseases.

Figure 1:
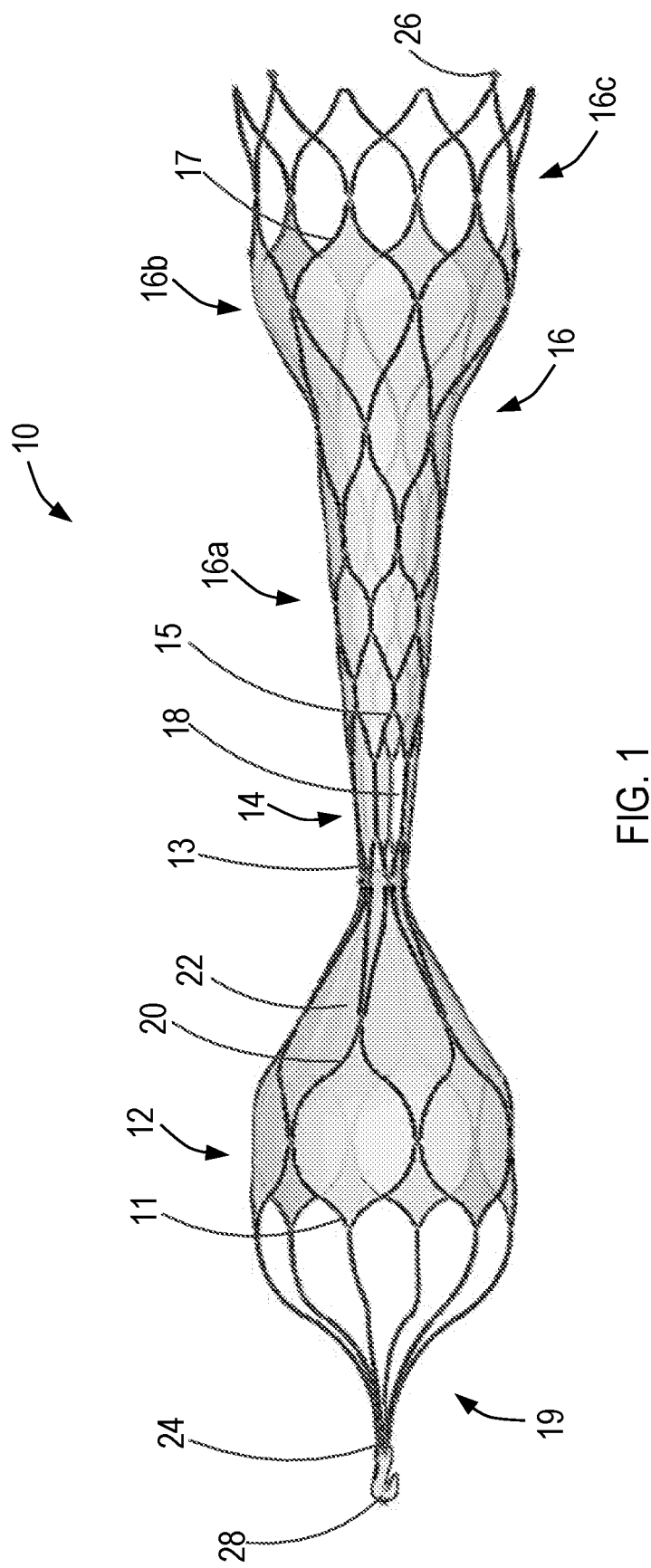
FIG. 1 is a side view of an exemplary fluid flow modulator constructed in accordance with the principles of the present invention.

Referring to FIG. 1, flow modulator 10 constructed and operative in accordance with the principles of the present invention is provided. Specifically, FIG. 1 is a side view of flow modulator 10 having upstream component 12, downstream component 16, and an entrainment region, e.g., gap 14, disposed between upstream component 12 and downstream component 16. The entrainment region may be integrally formed in downstream component 16 or in upstream component 12, or both. Gap 14 is designed to entrain fluid into a stream of fluid flowing from upstream component 12 to downstream component 16. As described below, upstream component 12 and downstream component 16 create a lower pressure region in the vicinity of gap 14, which preferably entrains fluid into the stream of fluid flowing across gap 14. Fluid entrainment is induced by shear-induced turbulent flux. In accordance with the principles of the invention, such entrainment is expected to transport blood or other body fluids to or from a region so as to improve organ function (e.g., from the renal vein(s) to the inferior vena cava to promote better functionality of the kidney(s) and/or from the hepatic vein(s) to the inferior vena cava to improve liver function, thereby treating disorders and/or diseases such as heart failure).

Upstream component 12 has inlet 11 and outlet 13, and has a cross-sectional flow area that converges in a downstream direction, e.g., from upstream component 12 towards downstream component 16, along part or all of the length of upstream component 12, thereby forming a nozzle. In this manner, upstream component 12 accelerates flow of fluid through upstream component 12. Downstream component 16 has entry 15 and exit 17, and has a cross-sectional flow area that diverges in a downstream direction along part or all of the length of downstream component 16, thereby forming a diffuser. As shown in FIG. 1, downstream component 16 may include first diverging portion 16a, second diverging portion 16b downstream from first diverging portion 16a, and uncovered portion 16c downstream from second diverging portion 16b. The average angle of divergence of second diverging portion 16b preferably is greater than the average angle of divergence of first diverging portion 16a. Uncovered portion 16c may be less rigid than the sealing zone of downstream component 16, and may adapt to the vessel without damaging the vessel, thereby preventing migration of flow modulator 10 during, e.g., coughing or other events that may cause a dramatic change in vessel diameter. Downstream component 16 thus decelerates flow of fluid through downstream component 16. The distance between outlet 13 and entry 15, e.g., the length of gap 14, is selected to generate a low pressure region in the vicinity of gap 14, while minimizing pressure loss and reducing resistance to fluid flow from the branch lumen(s), e.g., renal flow.

PCT International Patent Application Publications WO 2016/128983, WO 2018/029688, WO 2018/220589, WO 2019/097424, and WO 2020/109979, and U.S. Pat. No. 10,195,406 describe several converging and diverging structures that may be utilized as the flow modulator in accordance with the principles described herein, and the disclosures of each of those patents/applications are incorporated herein by reference in their entireties. Other converging and diverging structures suitable for use in accordance with the principles of the present invention are described herein. In addition, the present invention may be implemented using other kinds of converging and diverging structures, such as Stratford ramp nozzles (e.g., in which flow through the nozzle is on the verge of separation, which gives the diffuser the best length to efficiency ratio), de Laval nozzles (e.g., asymmetric hourglass shape), variable cross-sectional area nozzles and venturis, ramped nozzles and venturis, and others.

The central axis of the diverging portion may be disposed in-line with, or offset from, the central axis of the converging portion. As shown in FIG. 1, upstream component 12 and downstream component 16 share common, collinear flow axis. Alternatively, upstream component 12 may be angled with respect to downstream component 16. Upstream component 12 and downstream component 16 also may lie along a continuously curved path.

Upstream component 12 and downstream component 16 may be constructed as grafts, stents (coated or uncoated), stent grafts (coated or uncoated), and the like, and are formed of biocompatible materials, such as stainless steel or Nitinol. The outer contours of any of upstream component 12 and downstream component 16 may be sealed against the inner wall of the body lumen (such as by being expanded thereagainst), or alternatively may not be sealed, depending on the particular application. This may be referred to as the fixation area(s).

In accordance with one aspect of the present invention, flow modulator 10 is sized and shaped to be implanted in a body lumen. Flow modulator 10 may be compressed for delivery (e.g., percutaneous delivery within a delivery sheath) and expanded upon deployment (e.g., self-expanding upon release from the end of the delivery sheath or balloon expandable). Flow modulator 10 may be inserted into the body lumen in an antegrade or retrograde manner and similarly may be removed antegrade or retrograde. Flow modulator 10 may be used as an acute device to be removed after few hours/days or a chronic permanent device or a device that can be retrieved after long-term implantation. Additionally, flow modulator 10 may be decoupled from the delivery device and left in the patient for, e.g., 1-5 days or preferably 3 days, before retrieval and removal from the patient's body. When used as an acute device, flow modulator 10 may remain coupled to a delivery/retrieval device, e.g., sheath and/or wire/shaft, throughout the short-term implantation for ease of device delivery and retrieval, as described in further detail below. Flow modulator 10 may be compressible while disposed within a body lumen to allow periodic wash-out of stagnant flow zones created adjacent to flow modulator 10. For example, flow modulator 10 may be partially or fully reduced in diameter within the body lumen to allow blood flow through a stagnant flow zone.

Preferably, upon expansion, flow modulator 10 is sized to contact the inner wall of the body lumen to anchor flow modulator 10 within the lumen. Specifically, upstream component 12 may have a fixation area sized for anchoring upstream component 12 within the body lumen in its expanded, deployed state. For example, the fixation area of upstream component 12 may be sized to contact the inner wall of the body lumen and preferably has a diameter the size of, or slightly larger than, the diameter of the body lumen. The fixation area of upstream component 12 may have a constant diameter for a length suitable for anchoring upstream component 12 in the body lumen. Similarly, downstream component 16 may have a fixation area sized for anchoring downstream component 16 within another portion of the body lumen. For example, the fixation area of downstream component 16 may include at least a portion of second diverging portion 16b and/or uncovered portion 16c of downstream component 16. The fixation area of downstream component 16 may be sized to contact the inner wall of the other portion of the body lumen and preferably has a diameter the size of, or slightly larger than, the diameter of that portion of the body lumen. The fixation area of downstream component 16 may have a constant diameter for a length suitable for anchoring downstream component 16 in the body lumen. Preferably the fixation areas of upstream component 12 and downstream component 16 are configured to seal fluid modulator 10 within the body lumen so that fluid only flows into the fluid channels created by fluid modulator 10 and does not flow between the fixation areas of upstream component 12 and downstream component 16 and the vessel wall.

Flow modulator 10 may be formed from one or more frames and may be coated with one or more biocompatible materials. For example, the frame(s) may be formed of a metal (e.g., shape memory metal) or alloy or a combination thereof (e.g., a stent made of stainless steel or Nitinol or cobalt chromium). For some applications, the frame(s) may include a braided stent. In the case of more than one frame, the frames may be joined together by a suitable technique, such as welding. For example, upstream component 12 and downstream component 16 may be formed from a common frame or two frames that may be joined prior to implantation.

Flow modulator 10 may be constructed from frame 20 forming a plurality of cells, and frame 20 of flow modulator 10 may be at least partially coated with biocompatible material 22. As shown in FIG. 1, flow modulator 10 may be only partially covered with biocompatible material 22 such that a plurality of cells upstream of inlet 13, a plurality of cells forming uncovered portion 16c, and a plurality of cells at gap 14 remain uncoated. Specifically, upstream component 12 may be coated with biocompatible material 22 to define the fluid flow channel through upstream component 12, such that fluid flowing through a body lumen enters inlet 11, accelerates through the converging portion of upstream component 12, and exits out outlet 13 into the entrainment region of fluid modulator 10 having gap 14. A low pressure region is formed at gap 14 by the shapes of upstream component 12 and downstream component 16. Additional fluid from the branch lumen(s) at gap 14 is entrained into the fluid stream passing from outlet 13 to entry 15, via plurality of openings 18 formed by the uncoated portions at gap 14. Downstream component 16 also may be coated with biocompatible material 22 to define the fluid flow channel through downstream component 16, e.g., first diverging portion 16A and second diverging portion 16B, such that the fluid stream from outlet 13 together with the additional fluid passing through plurality of openings 18 at gap 14 enter entry 15, decelerate through the diverging portion of downstream component 16, and exit out exit 17 back into the body lumen, e.g., across uncovered portion 16c, which remains uncoated as described in further detail below.

Biocompatible material 22 may be a fabric and/or polymer such as expanded polytetrafluoroethylene (ePTFE), woven, knitted, and/or braided polyester, polyurethane, DACRON (polyethylene terephthalate), silicone, polycarbonate urethane, or pericardial tissue from an equine, bovine, or porcine source. The biocompatible coating may impede or block fluid flow where applied to the frame. The order of the joining and coating processes may be joining before coating or coating before joining. Biocompatible material 22 may be coupled to the frame(s) via stitching, spray coating, encapsulation, electrospinning, dip molding, and/or a different technique.

Alternatively, flow modulator 10 may be coated with a hydrophilic, hemocompatible coating (active such as heparin coating or passive) or a drug coating. In addition, flow modulator 10 may be selectively coated in different areas. For example, flow modulator 10 may include a drug coating on the sealing zones (the portions of flow modulator 10 that contact tissue) to prevent tissue adhesion to the IVC wall, and a heparin coating on the portions of flow modulator 10 where there is constant contact with blood to thereby prevent thrombus formation.

In a preferred embodiment, biocompatible material 22 is fluid impermeable. However, for some applications, the surfaces need not be impermeable, but may have a permeability that is sufficiently low as to substantially prevent blood from flowing through the longitudinal portion of the body lumen via any flow path other than through the flow channel defined by the inner surfaces of flow modulator 10. For some applications, each of the surfaces has permeability per unit length of less than 0.25 micrometers (e.g., between 0 and 0.25 micrometers), where the permeability per unit length is defined based upon the following equation, which is based upon Darcy's Law: $k/\Delta x = V\mu/\Delta p$, where k is permeability, $\Delta x$ is length (in meters), V is average velocity (in meters per second), $\mu$ is fluid viscosity (measured in Pascal-seconds), and $\Delta P$ is the pressure differential measured in Pascals).

Although the invention is not bound by any theory, a simplified engineering explanation is now provided to help understand how upstream component 12 and downstream component 16 operate to create reduced pressure at gap 14.

The Bernoulli equation governs the relationship between fluid velocity and pressure (neglecting the height difference):

$$P_1 + \tfrac{1}{2} \cdot \rho \cdot V_1^2 = P_2 + \tfrac{1}{2} \cdot \rho \cdot V_2^2 + E_{loss}$$

P=pressure
ρ=density
V=velocity
1=conditions at the inlet (upstream component 12)
2=conditions at gap 14
Mass conservation (same flow rate):

$$V_1 \cdot A_1 = V_2 \cdot A_2$$

A=Flow cross section
$E_{loss}$=Energy loss
For example, if flow modulator 10 is installed near the kidneys with upstream component 12 in the inferior vena cava, then $V_1$ and $A_1$ are the velocity and flow area, respectively, at the inferior vena cava.

The flow velocity at the gap ($V_2$) is designed to achieve the desired pressure reduction. For example, for 0.5 meter per second velocity and 3 times area ratio, a suction of about 6-8 mm Hg can be achieved. In the case of deployment near the kidney, this pressure differential is expected to improve renal function by improving renal perfusion pressure. The pressure will change due to improvement in the renal flow.

Applicant has discovered that using a maximum distance between the outlet of the upstream component and the entry to the downstream component will improve flow rates in the branched vessel(s) with relatively low pressure loss. A distance too great will create a significant pressure loss that actually sends flow in the wrong direction in the renal vein(s). In addition, other structural characteristics of the downstream component improve renal flow with low pressure loss such as a greater inner diameter at the entry of the downstream component than the inner diameter at the outlet of the upstream component, a greater length of the diverging area of the downstream component than the length of the converging area of the upstream component, and/or a lesser average angle of divergence of the downstream component than the average angle of convergence of the upstream component.

In another example, flow modulator 10 may be installed near a bifurcation to divert emboli from the bifurcation. In yet another example, flow modulator 10 may be deployed in the aortic arch to reduce peak systolic pressure.

The dimensions of flow modulator 10 may be suitable for implantation in the inferior vena cava. In particular, inlet 11 of upstream component 12 may be configured to be disposed upstream from a branch off to a renal vein(s), downstream component 16 may be configured to be disposed in the inferior vena cava, such that exit 17 is downstream from the branch off to the renal vein(s), and gap 14 may be disposed in the vicinity of the branch to the renal vein(s). Accordingly, the diameter of inlet 11 in the deployed, expanded state may range from 12-40 mm. The diameter of outlet 13 of upstream component 12 may be selected to create a jet velocity for a given device resistance. In the example of chronic cases, the diameter of outlet 13 may range from 3.5-8 mm. In acute cases, the diameter of outlet 13 preferably ranges from 3-7 mm. Moreover, flow modulator 10 may have an outer diameter at its upstream and downstream sealing zones ranging from 15 to 40 mm, and preferably 20 to 30 mm, and an overall length between 100-200 mm, and preferably 150 mm.

The length of the fixation area of upstream component 12 may range from 5-30 mm. The overall length of upstream component 12 may range from 15-60 mm. In accordance with the principles of the present invention, a shorter distance from outlet 13 of upstream component 12 to entry 15 of downstream component 16 will provide better performance for downstream component 16, but will result in lower renal flow because there is a greater resistance to flow from the renal vein(s) to downstream component 16. Thus, the distance from outlet 13 to entry 15 preferably is selected (e.g., in a range from −5-25 mm) to provide improved renal flow rate with minimal pressure loss.

The distance from outlet 13 of upstream component 12 to a center line of the branched lumen, e.g., the right renal vein, and may range from −25 mm to 100 mm. The length of the fixation area of downstream component 16 may range from 5-30 mm. The overall length of downstream component 16 is preferably greater than the overall length of upstream component 12 because a diverging shape creates a much higher pressure loss than a converging shape. For example, the length of first diverging portion 16A alone may be greater than the length of upstream component 12. The ratio of the overall length of upstream component 12 and the overall length of downstream component 16 may range from 1:1 to 3:1. The diameter at entry 15 of downstream component 16 is preferably larger than the diameter at outlet 13 of upstream component 12. Thus, the cross-sectional flow area at outlet 13 of upstream component 12 is less than the cross-sectional flow area at entry 15 of downstream component 16. The diameter at entry 15 of downstream component 16 is selected to receive all the fluid jetted from outlet 13. The ratio of the diameter at entry 15 of downstream component 16 and the diameter at outlet 13 of upstream component 12 may range from 1:1 to 2:1. In addition, the diameter at entry 15 of downstream component 16 may be greater when the distance between outlet 13 and entry 15 is larger to ensure receipt of the fluid jetted from upstream component 12. The diameter of exit 17 in the deployed, expanded state and may range from 12-40 mm.

Moreover, the average angle of divergence in downstream component 16 and may range from 5-30 degrees. Preferably, the angle of divergence in downstream component 16 is less than the angle of convergence in upstream component 12, and is expected to prevent pressure loss. In addition, downstream component 16 should have slow change in area adjacent to entry 15, e.g., closer to the renal vein, as any additional pressure loss will reduce the inferior vena cava flow rate and thus will reduce the effectiveness of the device. The angle of divergence in downstream component 16 may be constant or may change along the length of downstream component 16. When the angle of divergence changes along the length, the angle of divergence is preferably smallest (e.g., in a range from 5-30 degrees) adjacent to entry 15. A slow change in the cross-sectional flow area adjacent to entry 15 is preferred because the fluid velocity decreases as the cross-sectional flow area increases, hence the pressure loss. Accordingly, the angle of divergence is smallest at entry 15 where the fluid flow is at maximum velocity within downstream component 16.

As shown in FIG. 1, flow modulator 10 may include retrieval portion 19 at the proximal end of upstream component 12, configured to facilitate retrieval of flow modulator 19. Retrieval portion 19 may include constricted section 24 at an upstream end of flow modulator 10. Constricted section 24 allows flow modulator 10 to remain coupled to a delivery system. In the expanded, deployed state, the cross-sectional area of retrieval portion 19 converges from inlet 11 to constricted portion 24, where retrieval portion 19 is coupled together near the center of the flow path. Retrieval portion 19 preferably is uncoated such that a fluid stream flows across the retrieval portion 19 and through inlet 11 into upstream component 12. Moreover, uncoated retrieval portion 19 may optionally serve as a filter, e.g., against thrombus and/or emboli in blood. As described above, the overall length of downstream component 16 is preferably greater than the overall length of upstream component 12 (not including retrieval portion 19). Thus, the length from inlet 11 to outlet 13 of upstream component 12 may be less than the length from entry 15 to exit 17 of downstream component 16.

As shown in FIG. 1, a retrieval device, e.g., hook 28, may be coupled to constricted portion 24 to pull retrieval portion 19 towards a delivery sheath to compress flow modulator 10 into the delivery sheath for retrieval as described in further detail below. Hook 28 may be coupled to constricted portion 24 as a separate component that is, e.g., molded, glued, compressed, welded, etc. to frame 20. In this manner a retriever, e.g., a hook or goose-neck snare device, may be coupled to hook 28 to pull retrieval portion 19 towards a delivery sheath to compress flow modulator 10 into the sheath for retrieval. Additionally, hook 28 may be pulled in a direction(s) away from gap 14 to partially or fully reduce the diameter of flow modulator 10 within a body lumen. Such reduction would allow for wash-out of any stagnant flow zones created adjacent to flow modulator 10. Flow modulator 10 could then be fully removed, repositioned within the body lumen and expanded, or expanded in the prior deployment location within the body lumen.

In accordance with one aspect of the present invention, the downstream-most portion of downstream component 16 may form an atraumatic end of flow modulator 10 to prevent vessel damage and flare out during device crimping, and to give the distal end integrity. In the expanded, deployed state, the atraumatic end curves inward away from the body vessel inner wall. Accordingly, even after downstream component 16 is in its expanded, deployed state, flow modulator 10 may be readjusted within the body lumen with a reduced risk of injury to the vessel wall of the body lumen due to the distal end of flow modulator 10. In this embodiment, the cells formed by the frame of flow modulator 10 adjacent to the atraumatic end preferably is uncoated as shown in FIG. 1, such that the fluid stream flows out through exit 17 of downstream component 16 and across the uncoated, bare-metal frame of the atraumatic tip without additional acceleration due to a convergence of the flow path.

In addition, flow modulator 10 may include plurality of anchors 26 radially spaced around a downstream end of downstream component 16. As described in further detail below, plurality of anchors 26 are configured to be coupled to a delivery device to maintain downstream component 26 in a collapsed delivery state upon exposure to a body lumen from a sheath of the delivery device to facilitate readjustment of flow modulator 10 within the body lumen. In addition, plurality of anchors 26 may function as a downstream component retrieval portion in addition to the retrieval portion of upstream component 12, such that flow modulator 10 may be retrieved from the jugular.

Figure 2A:
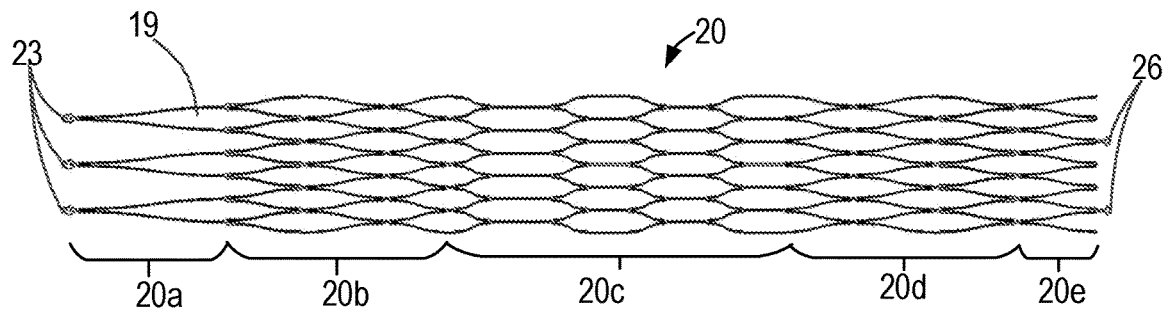
FIG. 2A illustrates the frame structure of the fluid flow modulator of FIG. 1.

Referring now to FIG. 2A, flow modulator 10 may be formed from a single frame structure 20. FIG. 2A illustrates frame 20 as cut and flattened to show the frame cutting pattern. Illustratively, upstream component 12 and downstream component 16 are defined by frame 20. Frame 20 is preferably formed from a metal tube that is laser cut to define a plurality of cells and then processed (e.g., heated) to form the shape of flow modulator 10. Retrieval portion 19 is illustratively formed from first plurality of cells 20a, e.g., with no junctions from eyelets 23 to the sealing zone of upstream component 12 to thereby prevent flow disruption. For example, frame 20 may include straight struts extending from eyelets 23 toward inlet 11 without any junctions therebetween. Upstream component 12 is illustratively formed from second plurality of cells 20b. Downstream component 16 is formed from two different configurations of cells. First diverging portion 16a of downstream component 16 may be formed from third plurality of cells 20c and second diverging portion 16b may be formed from fourth plurality of cells 20d. Third plurality of cells 20c preferably is disposed between second plurality of cells 20b and fourth plurality of cells 20d. Uncovered portion 16c may be formed from fifth plurality of cells 20e.

The void space may be the area of the cell defined by the struts of the frame. For example, the struts may define close-looped shapes therewithin, such as ellipses or diamonds or a combination thereof. The cells of plurality of cells 20b, 20c, 20d may be constructed as described in WO 2020/109979, the entire contents of which is incorporated by reference in its entirety herein. For example, the average void space area of second plurality of cells 20b may be larger than the average void space area of third plurality of cells 20c, and may be substantially identical to the average void space area of fourth plurality of cells 20d to create a more flexible structure than third plurality of cells 20c. Thus, frame 20 may be a three-part stent forming a flexible/rigid/flexible configuration. In addition, third plurality of cells 20c may include larger, yet more rigid cell shapes (e.g., elongated hexagonal shaped cells), and second plurality of cells 20b and fourth plurality of cells 20d may include smaller, yet more flexible cell shapes (e.g., diamond shaped cells).

Advantageously, after implantation, the flexible regions can change in diameter responsive to changes in vessel diameter while the more rigid portion of the stent structure remains constant. For example, the maximum outer diameter of upstream component 12 and downstream component 16 may change in diameter responsive to changes in vessel diameter while the shape of the outlet of the nozzle of upstream component 12 and/or the intermediate section (e.g., first diverging portion 16a) of flow modulator 10 does not change. In this manner, the angle of divergence of first diverging portion 16a may remain constant even though the size of the vessel changes. The change in diameter in the vessel may be measured, e.g., with one or more sensors on flow modulator and/or using imaging guidance such as fluoroscopy, to evaluate the diameter change over time.

As an additional or alternative way to enhance rigidity of the intermediate section of flow modulator 10, the struts of frame 20 at the intermediate section may be wider and/or thicker than the struts of frame 20 at the more flexible portions. For example, the struts of frame 20 may be wider and/or thicker at the section forming third plurality of cells 20c than at the sections forming second plurality of cells 20b and/or fourth plurality of cells 20d. Additionally or alternatively, the lengths of the cells formed by the struts of frame 20 may be shortened and/or the number of cells for a given length of frame 20 may be decreased to increase rigidity.

In accordance with another aspect of the present invention, the relative flexibility between the portions of the frame may be selected using different shaped cells, e.g., diamond shape or hexagonal shape. For example, the flexibility of second plurality of cells 20b and fourth plurality of cells 20d, and the rigidity of third plurality of cells 20c, may be selected based on the shape of the respective void space defined by the struts of frame 20 (e.g., flexibly-shaped cells/rigidly-shaped cells/flexibly-shaped cells in the frame). In addition, the cells having larger overall void space area may be stronger than the cells having a larger overall working area. Accordingly, the plurality of cells defining gap 14, e.g., third plurality of cells 20c, may have an overall larger average void space area while maintaining desired rigidity, such that a gap may be formed larger within a respective cell, thereby increasing the amount of flow that can be entrained through the gap than could be through a gap within a smaller diamond shaped cell.

Figure 2B:
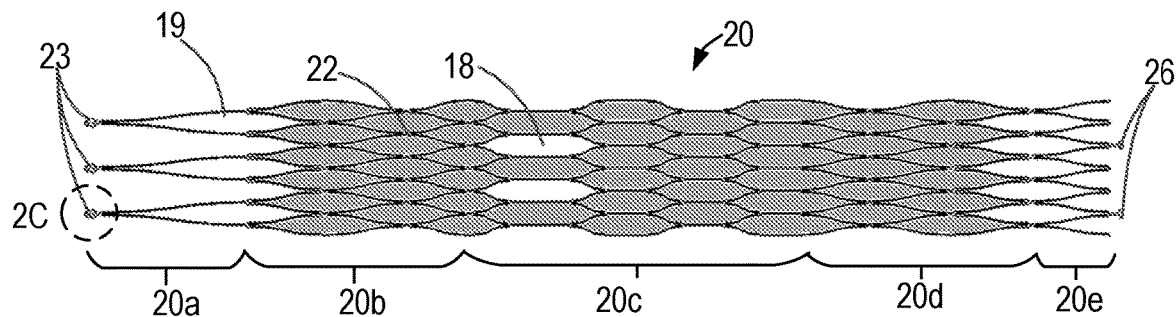
FIG. 2B illustrates the frame structure of FIG. 2A having selectively coated portions of biocompatible material in accordance with the principles of the present invention.

As shown in FIG. 2B, frame 20 may be at least partially coated with biocompatible material 22 denoted by the shaded void space areas, to thereby define inlet 11, exit 17, and plurality of openings 18. As described above, plurality of openings 18 at gap 14 may be defined by the uncoated plurality of cells between upstream component 12 and downstream component 16. For example, frame 20 of flow modulator 10 may initially be entirely coated with biocompatible material 22, and then selected portions of the coating may be removed, e.g., via cutting, melting, laser, chemical, etc., to form gap 14 and/or uncovered portion 16c. Accordingly, at least a portion of frame 20 forming gap 14 and/or uncovered portion 16c may remain partially coated with biocompatible material 22 after selected portions of the coating are removed. Alternatively, the frame of flow modulator 10 may be selectively coated such that portions that are not coated define plurality of openings 18 at gap 14 and/or uncovered portion 16c during the coating process. Accordingly, openings 18 and/or uncovered portion 16c may not be coated during the coating process. As shown in FIG. 2B, plurality of openings 18 may include uncoated portions along a single row of cells that define a plurality of longitudinally extending openings radially spaced around the entrainment region. Moreover, a pattern of the plurality of uncoated cells of gap 14 forming plurality of openings 18 may be selected to improve entrainment properties of fluid through gap 14 when in use in a blood vessel.

Fifth plurality of cells 20e are shaped such that uncovered portion 16c is more flexible than second diverging portion 16b, e.g., the sealing zone of downstream component 16. Accordingly, uncovered portion 16c may adapt to the vessel without damaging the vessel, e.g., when the vessel is small, and further prevent migration of flow modulator 10 during, e.g., coughing or other events that may cause a dramatic change in vessel diameter.

As shown in FIGS. 2A and 2B, the distal end of fifth plurality of cells 20e may include one or more anchors 26 for assisting in maintaining downstream component 16 in its collapsed, delivery state upon exposure from a delivery sheath, as described in further detail below. In accordance with another aspect of the present invention, frame 20 does not include anchors 26, and the uncoated, bare-metal portion of fifth plurality of cells 20e forming the distal end of downstream component 16 may be used to maintain downstream component 16 in its collapsed, delivery state upon exposure from the delivery sheath.

Figure 2C:
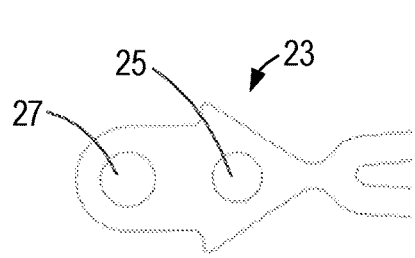
FIG. 2C is a close up view of an eyelet of the frame structure of FIG. 2B.
Figure 2D:
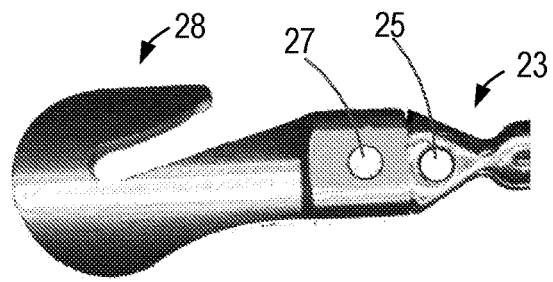
FIG. 2D illustrates a hook coupled to the eyelet of FIG. 2C in accordance with the principles of the present invention.

As shown in FIGS. 2A and 2B, retrieval portion 19 of upstream component 12 may include one or more eyelets 23, e.g., pushers or pullers, to facilitate deployment and/or retrieval of flow modulator 10 from a compressed state within the delivery sheath to an expanded state outside of the delivery sheath when force is exerted on hook 28. FIG. 2C is a close-up view of eyelet 23 of FIG. 2B. As shown in FIG. 2C, eyelet 23 may include hole 25 for facilitating attachment of hook 28 to eyelet 23. Hole 25 may subsequently be filled or intentionally left empty during operation. In addition, eyelet 23 may include pin 27 sized and shaped to engage with a corresponding hole of hook 28 for securing hook 28 to eyelet 23, e.g., via welding, glue, riveting, or press fit, as shown in FIG. 2D. As shown in FIG. 2D, the angled surface of eyelet 23 may provide a smooth transition at the engagement point between hook 28 and eyelet 23, thereby preventing a retrieval device, e.g., a snare, from being caught therebetween. In the expanded, deployed state, the retrieval portion of upstream component 12 may converge from inlet 11 towards constricted section 24, and thus, one or more eyelets 23 may meet together at constricted section 24 where they may be coupled to hook 28. Accordingly, when retrieval portion 19 of upstream component 12 includes more than one eyelet 23, all the eyelets may be coupled to hook 28.

Figure 3A:
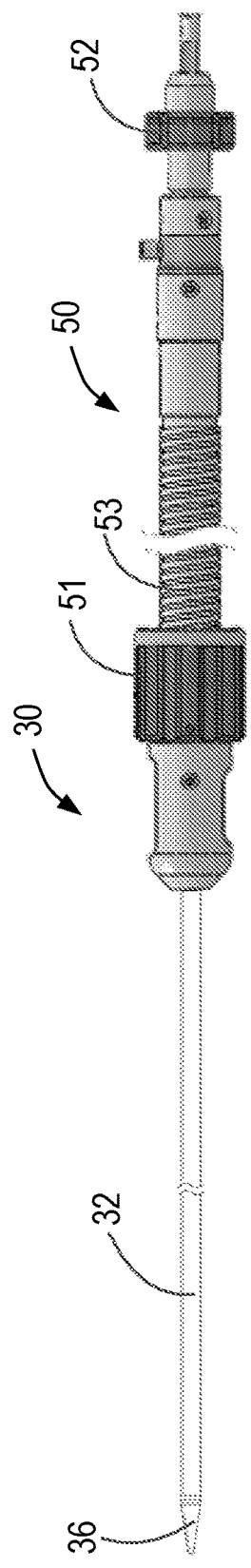
FIGS. 3A-3G are schematic illustrations of an exemplary delivery device that is configured to deploy a flow modulator within a body lumen, constructed in accordance with the principles of the present invention.
Figure 3B:
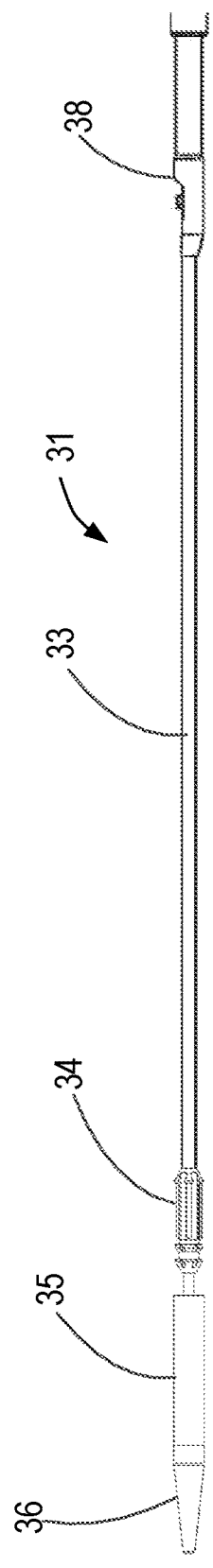
Figure 3C:
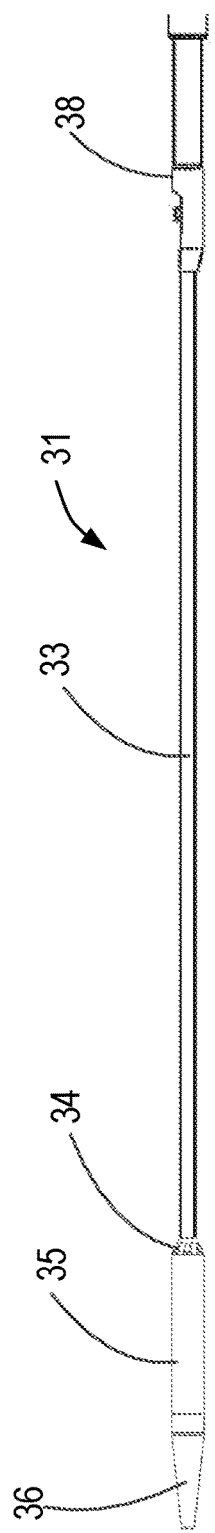

Referring now to FIGS. 3A to 3C, delivery device 30 for delivering flow modulator 10 to the body lumen is described.

As shown in FIG. 3A, delivery device 30 may include handle 50 operatively coupled to the proximal end of sheath 32 having a lumen of suitable size to hold flow modulator 10 in a collapsed, delivery state, and inner assembly 31 slidably disposed within the lumen of sheath 32 and removeably coupled to flow modulator 10. As shown in FIGS. 3B and 3C, delivery device 30 may include inner assembly 31 operatively coupled to handle 50 to facilitate deployment of flow modulator 10 through the distal end of sheath 32. Sheath 32 may include a radiopaque marker at its distal end to aid in visualization.

Handle 50 allows a clinician to hold and maneuver sheath 32 and inner assembly 31, and optionally for coupling to a hose for flushing out the lumen of sheath 32. As shown in FIG. 3A, handle 50 may include a plurality of actuators, e.g., knob 51 rotatably slidable along the threaded surface of rod 53 for actuating, e.g., sheath 32, and knob 52 for actuating outer cover 35 to deploy the distal end of flow modulator 10 as described in further detail below. Accordingly, handle 50 may be actuated to move inner assembly 31 relative to sheath 32 to retract sheath 32 and/or push flow modulator 10 through the lumen of sheath 32 and out a distal end of sheath 32. In addition, handle 50 may include a flush port for flushing of crimped flow modulator 10.

Figure 3D:
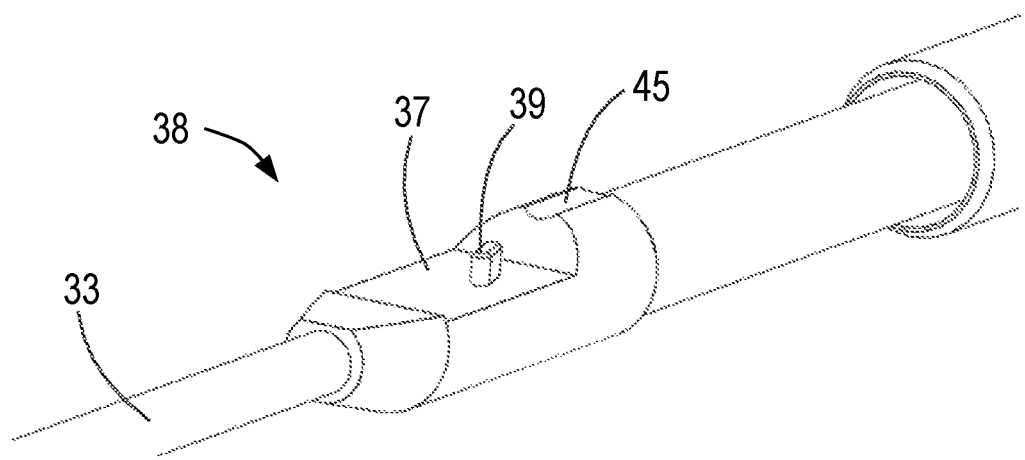
Figure 3E:
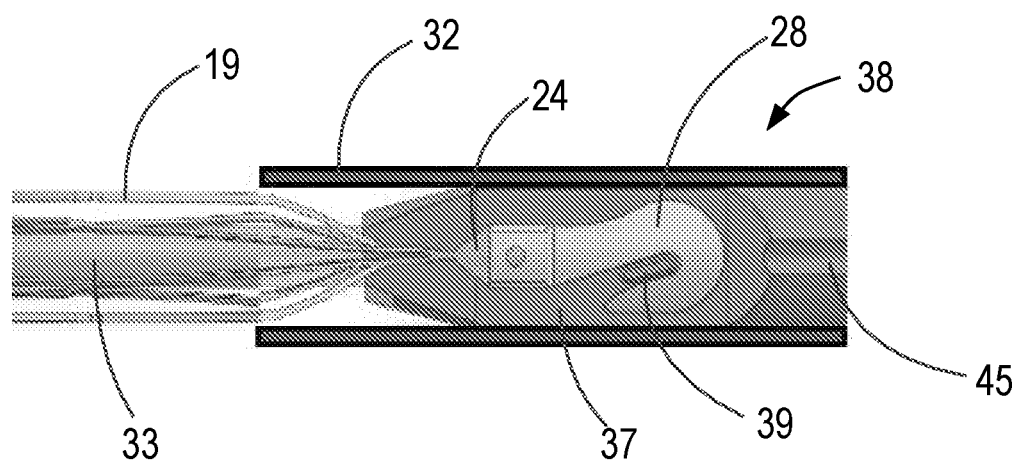

As shown in FIGS. 3B and 3C, inner assembly 31 may include rod 33, which may be coupled to retriever 38 at its proximal end, and coupled to mount 34 at its distal end. Rod 33 may be a hypotube that provides flexibility while maintaining pushability. As shown in FIGS. 3D and 3E, retriever 38 may include cut-out portion 37 and protrusion 39 disposed within cut-out portion 37, sized and shaped to receive hook 28 as shown in FIG. 3E. For example, cut-out portion 37 may include an angled proximal wall to facilitate detachment of hook 28 from retriever 38 when delivery device 30 is pushed forward relative to flow modulator 10. Accordingly, when sheath 32 is disposed over hook 28 and constricted section 24 while hook 28 is engaged with protrusion 39, the proximal end of flow modulator 10 will remain engaged with inner assembly 31. Thus, retriever 38 may be coupled to and remain coupled to constricted section 24 of flow modulator 10, e.g., via hook 28, during an acute treatment. Alternatively, retriever 38 may be a separate device slidably disposed within the lumen of sheath 32 for coupling with constricted section 24 of flow modulator 10, e.g., a hook or a snare device. In addition, retriever 38 may include groove 45 sized and shaped to permit high flow of a contrast medium from deliver device 30 while hook 28 is engaged with protrusion 39 within sheath 32, to thereby confirm location of flow modulator 10 while flow modulator 10 is still coupled to delivery device 30.

Figure 3F:
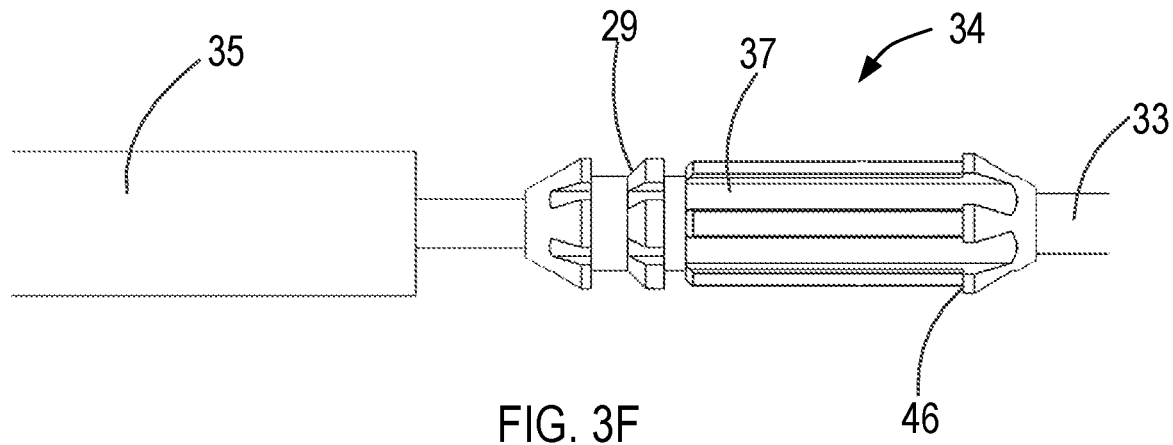
Figure 3G:
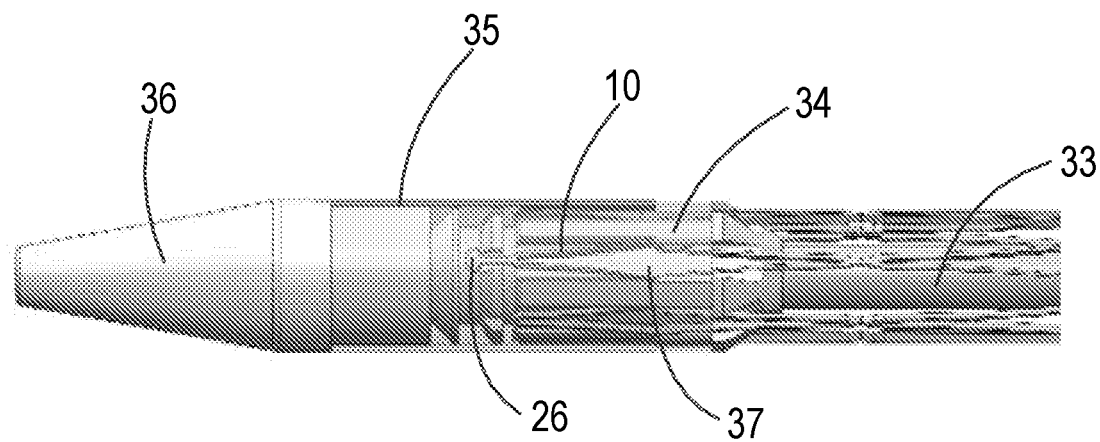

As shown in FIGS. 3F and 3G, inner assembly 31 may include mount 34 coupled to the distal end of rod 33, and outer cover 35 coupled to end cap 36 and slidably moveable over at least a portion of mount 34. Mount 34 and outer cover 35 may both be sized with fit within the lumen of sheath 32, and the distal portion of end cap 36 may have an outer diameter substantially equal to the outer diameter of sheath 32 such that sheath 32 may receive mount 34 and outer cover 35 therein during delivery, but not the distal portion of end cap 36. Accordingly, end cap 36 may be removably coupled to the distal end of sheath 32 to create a seal for the lumen of sheath 32 during delivery.

As shown in FIGS. 3F and 3G, mount 34 includes a plurality of receptacles 37 sized and shaped to receive and releasably engage with plurality of anchors 26 of uncovered portion 16c of downstream component 16 of flow modulator 10. For example, plurality of anchors 26 of downstream component 16 may be received by plurality of receptacles 37 of mount 34, such that anchor 26 engages with sloped portion 29 of mount 34. Sloped portion 29 is angled such that flow modulator 10 may disengage from mount 34 and be deployed while fully stretched out within sheath 31. Preferably, sloped portion 29 has an angle of 10-80 degrees from the longitudinal axis of rod 33. Accordingly, plurality of anchors 26 may include a "T" shaped projection sized and shaped to hold mount 34 during crimping.

Outer cover 35 may be disposed over plurality of receptacles 37 to thereby engage plurality of anchors 26 and maintain downstream component 16 in its collapsed, delivery state. Accordingly, mount 34 may include stopper portion 46 having an outer diameter that prevents proximal movement of outer cover 35 relative to mount 34 beyond stopper portion 45. Outer cover 35 may be moved distally relative to mount 34, e.g., via knob 52 of handle 50, to expose plurality of anchors 26 such that plurality of anchors 26 disengage with plurality of receptacles 37 along sloped portion 29 to thereby transition, e.g., self-expand, downstream component 16 from its collapsed, delivery state to its expanded, deployed state. Accordingly, plurality of receptacles 37 may define recesses that match the shapes of plurality of anchors 26, and the frame of uncovered portion 16c of downstream component 16. Alternatively or additionally, plurality of receptacles 37 may include a hook mechanism for coupling with plurality of anchors 26 when outer cover 35 is disposed over plurality of receptacles 37. Accordingly, upon retraction of sheath 32 to expose flow modulator 10 out the distal end of sheath 32 within the body lumen, flow modulator 10 may be maintained in its collapsed, delivery state, to permit safe readjustment of flow modulator 10 within the body lumen without having to fully deploy flow modulator 10 and potentially injuring the body lumen.

In accordance with one aspect of the present invention, downstream component 16 may not require a plurality of anchors for engagement with plurality of receptacles 37. For example, uncovered portion 16c of downstream component 16 may be engaged with plurality of receptacles 37 within outer cover 35, and thus effectively function as a plurality of anchors.

Figure 4:
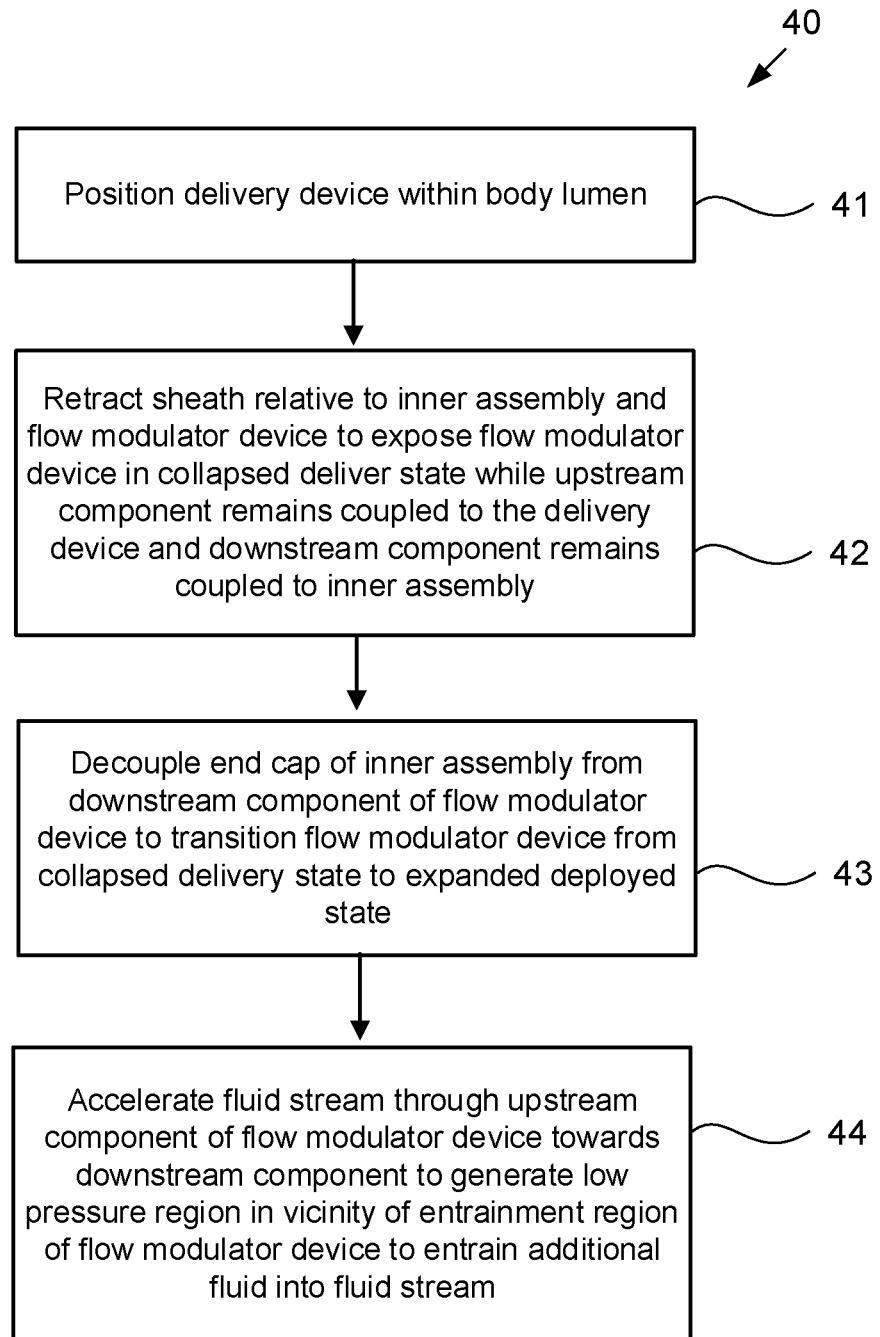
FIG. 4 is a flow chart illustrating the steps of an exemplary method for altering fluid flow through a body lumen in accordance with the principles of the present invention.

Referring now to FIG. 4, steps of exemplary method 40 for altering fluid flow through a body lumen using flow modulator 10 in accordance with the principles of the present invention is provided. Some of the steps of method 40 may be further elaborated by referring to FIGS. 5A-5F. First, under ultrasound guidance and using Seldinger technique, a guidewire may be placed in the right femoral vein. At step 41, delivery device 30 is introduced to a position within the patient's body lumen, e.g., adjacent the renal veins within the inferior vena cava (IVC). For example, following standard pre-dilatation, delivery device 30 may be placed over the guidewire introduced into the femoral vein and advanced up to the supra-renal IVC under fluoroscopy guidance. Deliver device 30 with loaded flow modulator 10 may be navigated to the target location which is identified by venogram as follows: distal sealing zone positioned between higher renal ostium and hepatic vein ostium; proximal sealing zone is positioned between lower renal ostium and iliac bifurcation; and proper vessel diameter sizing is maintained.

Figure 5A:
FIGS. 5A-5F illustrate the steps of an exemplary method for delivering a fluid flow modulator in accordance with the principles of the present invention.

Accordingly, the distal end of delivery device 30 may be positioned downstream of the renal veins within the IVC such that flow modulator 10 may be deployed to effectively entrain additional fluid from the renal veins to the fluid stream through the IVC. As shown in FIG. 5A, sheath 32 is coupled to end cap 36 such that mount 34 and outer cover 35 are disposed within the lumen of sheath 32, and flow modulator 10 is disposed within the lumen of sheath 32 in its collapsed, delivery state. In addition, plurality of anchors 26 of downstream component 16 are engaged with plurality of receptacles 37 of mount 34 within outer cover 35, and constricted section 24 of upstream component 12 is coupled to retriever 38 of delivery device 30, e.g., via protrusion 39 and hook 28, within sheath 32.

Figure 5B:
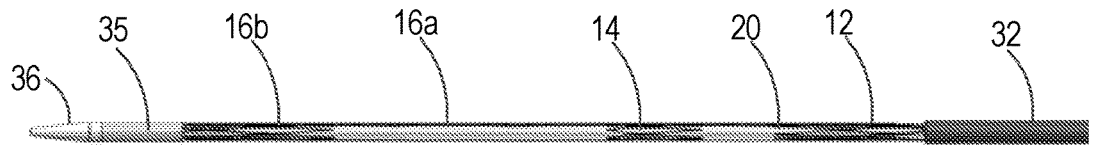

At step 42, sheath 32 is retracted proximally relative to inner assembly 31 and flow modulator 10 to expose flow modulator 10 out of the distal end of sheath 32 as shown in FIG. 5B. Constricted section 24 of flow modulator 10 may remain coupled to the delivery device within sheath 32, e.g., via hook 28 and/or retriever 38, when flow modulator 10 is exposed out of the distal end of sheath 32, thereby preventing premature expansion of flow modulator 10. Alternatively, constricted section 24 of flow modulator 10 may be decoupled from the delivery device when flow modulator 10 is exposed out of the distal end of sheath 32, thereby causing upstream component 12 to expand while downstream component 16 remains coupled to mount 34 within outer cover 35 in its collapsed, delivery state. In this embodiment, flow modulator 10 may be still be readjusted within the body lumen.

Figure 5C:
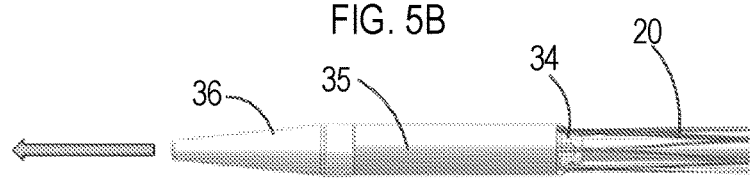

As shown in FIG. 5C, outer cover 35 is disposed over plurality of receptacles 37 of mount 34, such that plurality of anchors 26 of downstream component 16 is engaged with end cap 36 of delivery device 30 and flow modulator 10 remains in its collapsed, delivery state upon exposure from the lumen of sheath 32. As well be understood by a person of ordinary skill in the art, inner assembly 31 may be pushed distally relative to sheath 32 to expose flow modulator 10 out the distal end of sheath 32 within the body lumen. While flow modulator 10 is exposed from sheath 32 within the body lumen, the physician may readjust the position of flow modulator 10 via delivery device 30 within the body lumen until flow modulator 10 is in the desired position within the body lumen, without having to fully deploy flow modulator 10. Accordingly, flow modulator 10 may be readjusted within the body lumen without blocking/interfering with blood flow through the body lumen and without risk of injury to the vessel wall of the body lumen, e.g., via interaction between the vessel wall and the fixation areas of either upstream component 12 or downstream component 16 in their expanded, deployed state. Alternatively, downstream component 16 may not be coupled to end cap 32 such that when flow modulator 10 is exposed out of the distal end of sheath 32, downstream component 12 automatically transitions to its expanded, deployed state as described in WO 2020/109979, the entire contents of which is incorporated by reference in its entirety herein.

Figure 5D:
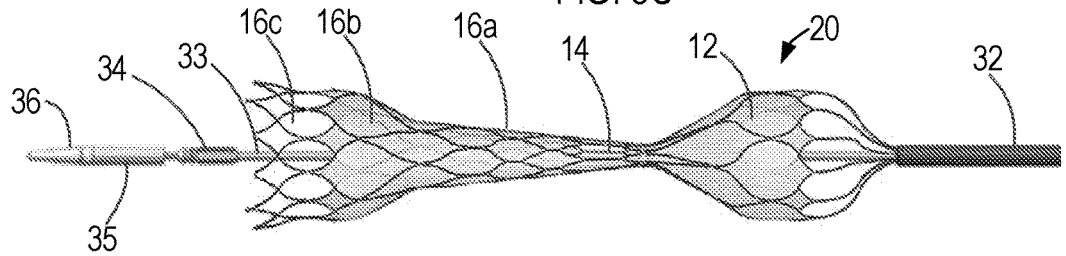

At step 43, end cap 36 of inner assembly 31 may be decoupled from downstream component 16 such that downstream component 16 self-expands from its collapsed, delivery state, to its expanded, deployed state, as shown in FIG. 5D. Specifically, outer cover 35 may be moved distally relative to mount 34 to expose plurality of receptacles 37 of mount 34 such that plurality of anchors 26 may disengage from plurality of receptacles 37 along sloped portion 29. As shown in FIG. 5D, upon expansion of downstream component 16, upstream component 12 is also permitted to self-expanded to its expanded, deployed state. Upon expansion of flow modulator 10 from its collapsed, delivery state to its expanded, deployed state, constricted section 24 may remain coupled to delivery device 30, e.g., via hook 28 and/or retriever 38, to permit re-sheathing of flow modulator 10 if necessary. For example, upon expansion of flow modulator 10, flow measurements may be taken to confirm that flow modulator 10 is properly positioned within the body lumen, e.g., by injecting contrast media to visualize flow across flow modulator 10. If it is determined that flow modulator 10 is not properly positioned, flow modulator may be re-collapsed within sheath 32 via hook 28 and/or retriever 38 such that flow modulator may be repositioned within the body lumen. When flow modulator 10 is chronically implanted, constricted section 24 may be decoupled from retriever 38 of the delivery device. Alternatively, constricted section 24 may remain coupled to delivery device 30, e.g., via hook 28 and/or retriever 38, throughout an acute treatment to facilitate retrieving flow modulator 10 after completion of the treatment.

Accordingly, at step 44, the fluid stream within the IVC may be accelerated through upstream component 12 of fluid modulator 10 towards downstream component 16 to generate a low pressure region in the vicinity of the entrainment region of flow modulator 10 to entrain additional fluid from the branch vessel, e.g., from the renal veins, into the fluid stream via gap 14 in accordance with the principles of the present invention described herein.

Figure 5E:
Figure 5F:
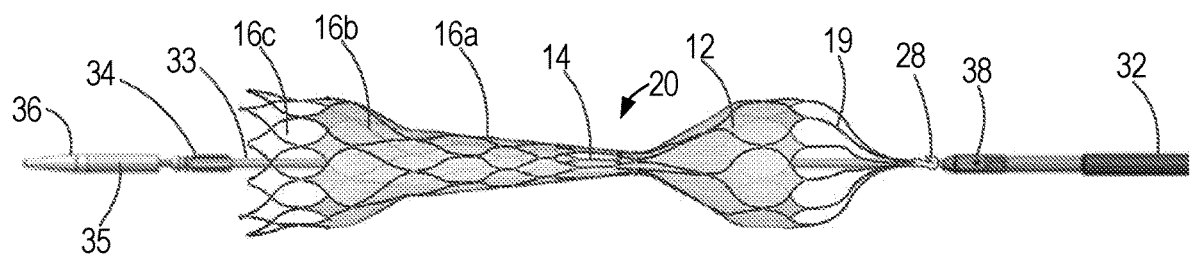

Alternatively, flow modulator 10 may be detached from delivery device 30 by further retracting sheath 32 proximally relative to inner assembly 31, as shown in FIGS. 5E and 5F, and left implanted for an amount of time (e.g., hours, days, months, years) for a chronic treatment. Specifically, constricted portion 24 may be decoupled from protrusion 39 of retriever 38 within sheath 32 to disengage flow modulator 10 from delivery device 30. Accordingly, delivery device 30 may be removed from the body lumen, leaving flow modulator 10 implanted within the body lumen. If implanted, flow modulator 10 may be retrieved by recoupling retriever 38 to hook 28 at constricted section 24, e.g., re-engaging hook 28 with protrusion 39 of retriever 38, and pulling hook 28 to collapse upstream component 12 of flow modulator 10 into its collapsed, delivery state. Hook 28 may further be retracted or sheath 32 may be advanced to receive flow modulator 10 within lumen of sheath 32 in its collapsed, delivery state. For example, sheath 32 may be moved distally while inner assembly 31 is held in place to transition flow modulator 10 from the expanded, deployed state to the collapsed, delivery state within sheath 32, until mount 34 and outer cover 35 are disposed within the lumen of sheath 32 and end cap 36 forms a seal with the distal end of sheath 32. In accordance with the principles of the present invention, when downstream component 16 is returned to its collapsed, delivery state, plurality of anchors 26 may reengage with plurality of receptacles 37 of mount 34 of end cap 36, and outer cover 35 may be disposed over plurality of receptacles 37 to maintain flow modulator 10 in its collapsed, delivery state. Delivery device 30 then may be moved proximally and out of the patient's body.

In accordance with one aspect of the present invention, a different retrieval system other than the retriever and delivery sheath used to deliver flow modulator 10 may be employed to retrieve flow modulator 10. For example, a separate snare device may be coupled to hook 28 to pull and collapse flow modulator 10 within a retrieval sheath. Alternatively, the snare device may be held in place when coupled to flow modulator 10, such that the retrieval sheath is advanced over flow modulator 10 and the snare device to collapse flow modulator 10 within the retrieval sheath.

As described in WO 2020/109979, the entire contents of which is incorporated by reference in its entirety herein, flow modulator 10 may transition to the expanded, deployed configuration when exposed past the distal end of sheath 32 using a stopper mechanism. For example, sheath 32 may be pulled proximally against a fixed stopper in sheath 32 to unsheath flow modulator 10 at a target location within a body lumen, e.g., where the renal veins intersect with the inferior vena cava.

Figure 6:
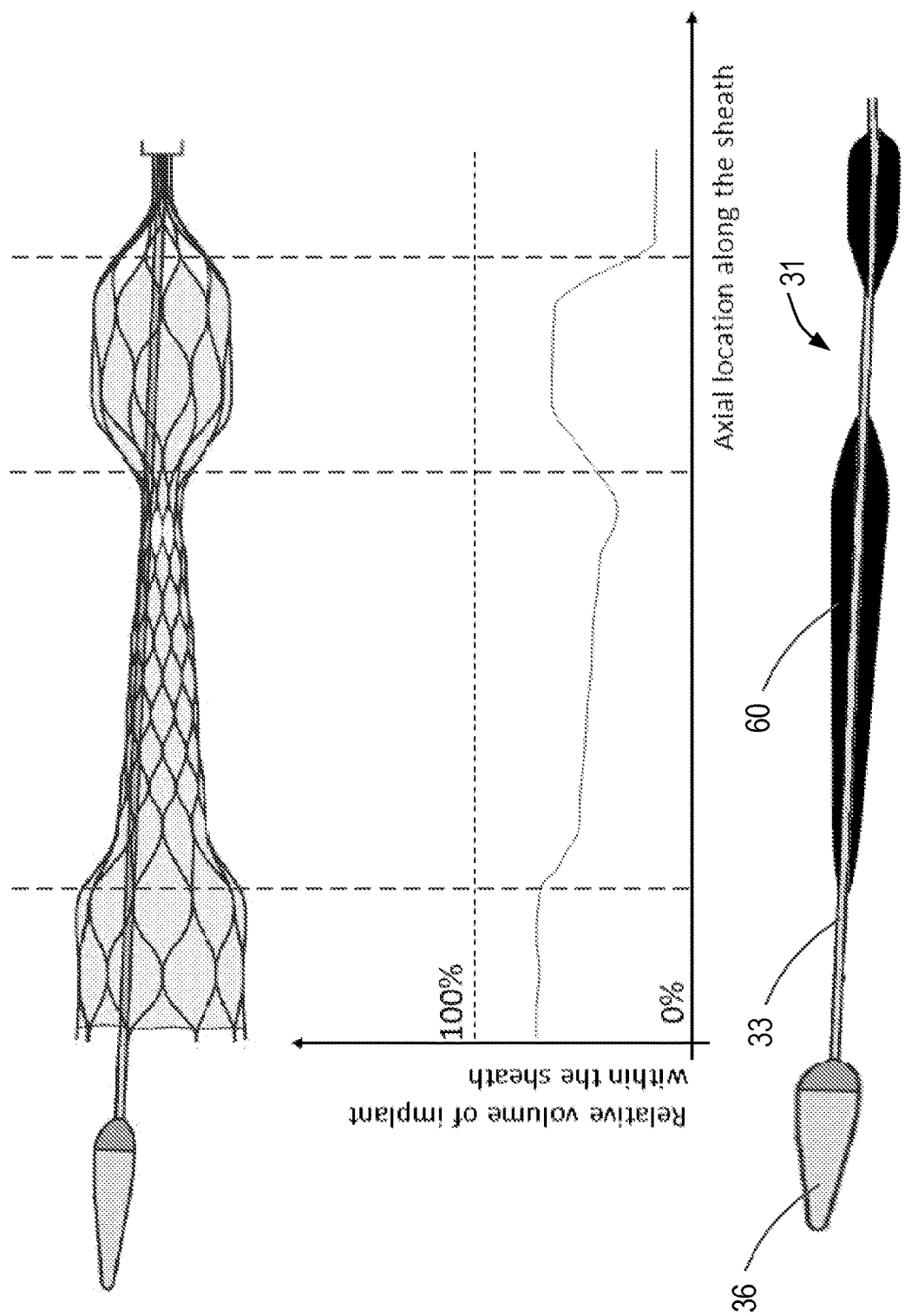
FIG. 6 illustrates the inner assembly of an exemplary delivery device constructed to prevent kinking of the fluid flow modulator during delivery within a sheath.

Referring now to FIG. 6, a volume curve of flow modulator 10 along its axial length when disposed within the lumen of sheath 32 in its collapsed, delivery state is provided. The relative volume of flow modulator 10 is the superposition of the metal stent frame, e.g., frame 20, and the biocompatible coating, e.g., biocompatible material 22. The volume of the frame is relatively constant along the axial length of flow modulator 10, regardless of the local diameter in its expanded, deployed state, as the frame may be cut from a tube having uniform thickness and diameter. The volume of the biocompatible coating has a positive relationship with the diameter of flow modulator 10 in its expanded, deployed state as the larger diameter portion will contain locally more coating. Thus, as shown in FIG. 6, the volume curve of flow modulator 10 along its axial length looks like the diameter profile of flow modulator 10 in its expanded, deployed state. In accordance with one aspect of the present invention, inner assembly 33 of delivery device 30 may include adaptive pattern 60 disposed along the axial length of rod 33 corresponding to the volume curve of flow modulator 10 in the collapsed, delivery state within sheath 32. Accordingly, adaptive pattern 60 may support flow modulator 10 in its collapsed, delivery state within sheath 32 to prevent kinking in low volume regions during deliver.

Figure 7:
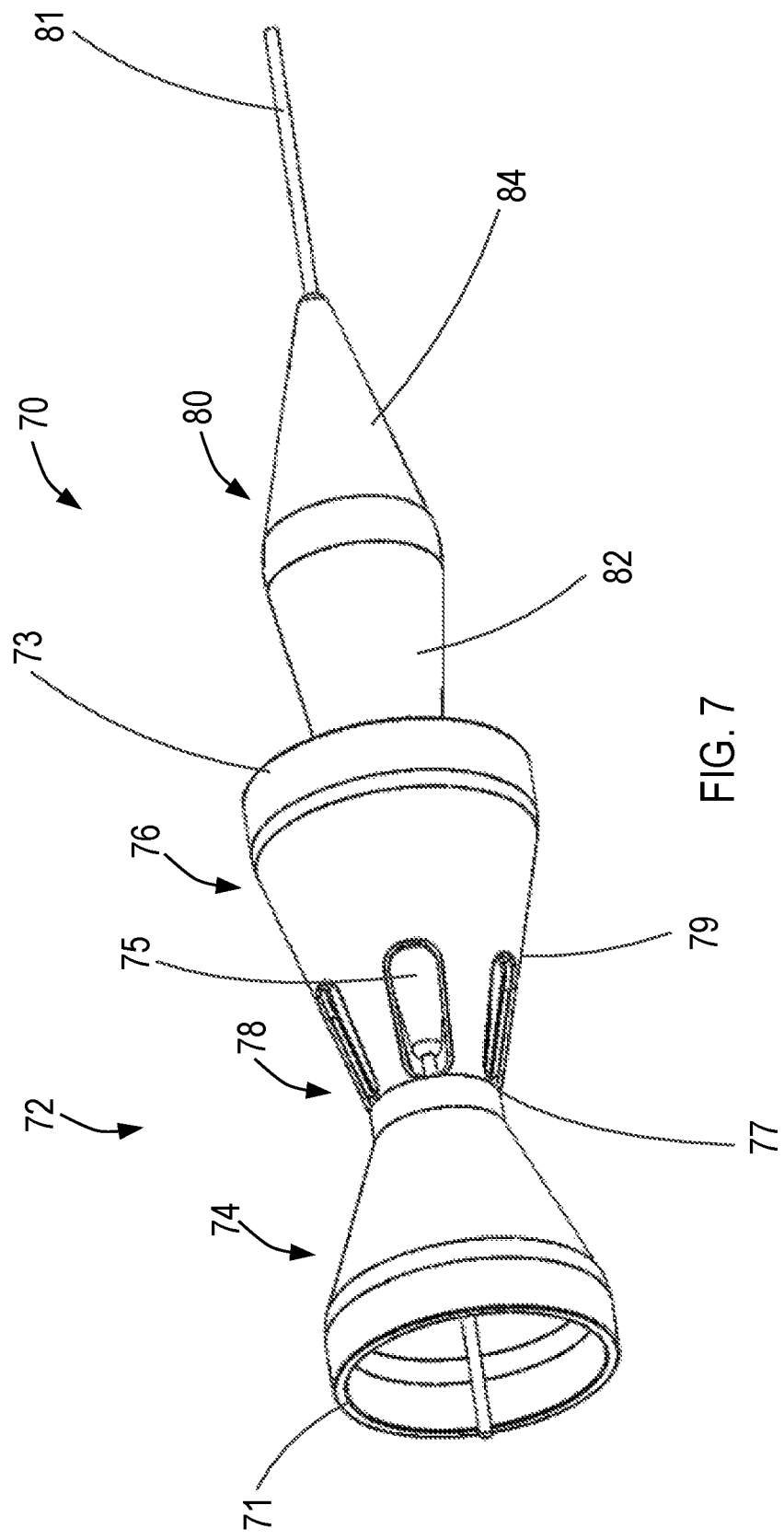
FIG. 7 is a schematic view of another exemplary fluid flow modulator constructed in accordance with the principles of the present invention.

Referring now to FIG. 7, another exemplary fluid flow modulator constructed in accordance with the principles of the present invention is provided. As shown in FIG. 7, flow modulator 70 includes hourglass-shaped stent 72 and core 80 slidably disposed within the passageway of stent 72. Stent 72 may be constructed similarly to flow modulator 10 of FIG. 1, except that downstream component 76 of stent 72 need not have two diverging portions having different divergence angles due to the presence of core 80, which acts as a diffuser within the body lumen. Accordingly, stent 72 may have a shorter overall length than flow modulator 10, e.g., a minimum total length of 3 cm.

Specifically, as shown in FIG. 7, stent 72 includes upstream component 74, downstream component 76, and an entrainment region, e.g., gap 78, disposed between upstream component 74 and downstream component 76. The entrainment region may be integrally formed in downstream component 76 or in upstream component 74, or both. As shown in FIG. 7, upstream component 74 has inlet 71 and outlet 77, and has a cross-sectional flow area that converges in a downstream direction, e.g., from upstream component 74 towards downstream component 76, along part or all of the length of upstream component 74, thereby forming a nozzle. In this manner, upstream component 74 accelerates flow of fluid through upstream component 74. Downstream component 76 has entry 79 and exit 73, and has a cross-sectional flow area that diverges in a downstream direction along part or all of the length of downstream component 76, thereby forming a diffuser. Like flow modulator 10, upstream component 74 and downstream component 76 may have fixation areas for contacting the inner wall of the blood vessel to maintain stent 72 in the desired positioned within the blood vessel. The fixation areas are the largest diameter portions of stent 72 which contact the vessel wall.

Like gap 14, gap 78 may include one or more openings 75 disposed radially about the entrainment region for entraining additional fluid therethrough. Accordingly, upstream component 74 and downstream component 76 create a lower pressure region in the vicinity of gap 78, which preferably entrains fluid into the stream of fluid flowing across gap 78 through openings 75. Openings 75 may extend radially away from a central longitudinal axis of stent 72 such that the distance between openings 75 and the axis gradually increases as openings 75 extends from outlet 77 to entry 79. This design maintains the benefits described with respect to flow modulator 10, while creating less resistance for the renal blood flow (RBF) and without impairing the diffuser's effect on the IVC jet flow. Moreover, as the overall length of stent 72 may be shorter, a smaller volume of blood will be positioned between upstream component 74 and downstream component 76 before entrainment via openings 75, thereby reducing risk of thrombus formation.

Core 80 includes upstream region 82 and downstream region 84. Upstream region 82 has a first end, e.g., the most upstream point of core 80, and a cross-sectional area that increases from the first end towards downstream region 84 such that upstream region 82 of core 80 diverges along the direction of IVC flow. Downstream region 84 has a second end, e.g., the most downstream point of core 80, and a cross-sectional area that decreases from upstream region 82 toward the second end such that downstream region 84 of core 80 converges along the direction of IVC flow. The cross-sectional area of upstream region 82 may increase at a smaller rate than the rate of decrease of the cross-sectional area of downstream region 84. Core 80 may have a maximum overall length of, e.g., 15 cm. In addition, core 80 may be symmetric about a longitudinal plane extending along the longitudinal axis of core 80. The thickness or diameter of core 80 may continuously change from the first end to the second end along the longitudinal axis of core 80, having a maximum cross-sectional area at the junction between upstream region 82 and downstream region 84.

Moreover, core 80 may be positioned within downstream component 76 and at least partially within upstream component 74 of stent 72 to manipulate the effective angle of the nozzle and the diffuser to achieve the desired flow through flow modulator 70, thus enhancing the IVC blood flow and RBF. For example, as shown in FIG. 7, core 80 may be coupled to catheter 81, which may be actuated to adjust the position of core 80 with respect to stent 72. The adjustability of core 80 relative to stent 72 allows flow modulator 70 to be used compatibly with all patients, regardless of their flow rates, and may be advantageous for both acute and chronic applications. Core 80 may block blood flow within the vessel lumen such that blood cannot flow through core 80, thereby forcing blood to flow only around core 80 within stent 72. Core 80 may be completely suspended within stent 72 and the vessel lumen without contacting any portion of the inner surface of stent 72 or the inner wall of the vessel.

Core 80 may be a compliant, non-compliant, or rigid body. In accordance with one aspect of the present invention, core 80 may be an inflatable balloon. Accordingly, the cross-sectional area of core 80 along upstream region 82 and downstream region 84 may be adjusted via inflation of core 80. For example, catheter 81 may include an inflation/deflation lumen in fluid communication with an interior of core 80 for inflating/deflating core 80. Accordingly, core 80 may be selectively inflated/deflated via inflation/deflation lumen(s) to achieve the desired IVC resistance.

Figure 8A:
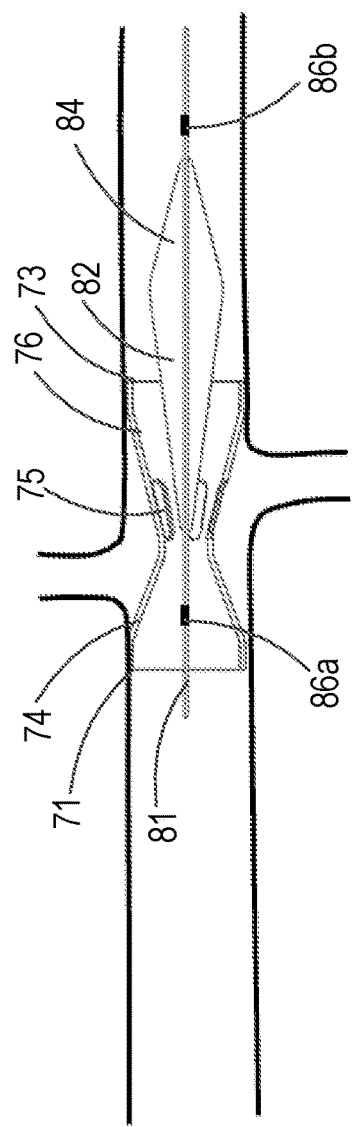
FIGS. 8A-8C are schematic views of the fluid flow modulator of FIG. 7 positioned within a body lumen in accordance with the principles of the present invention.
Figure 8B:
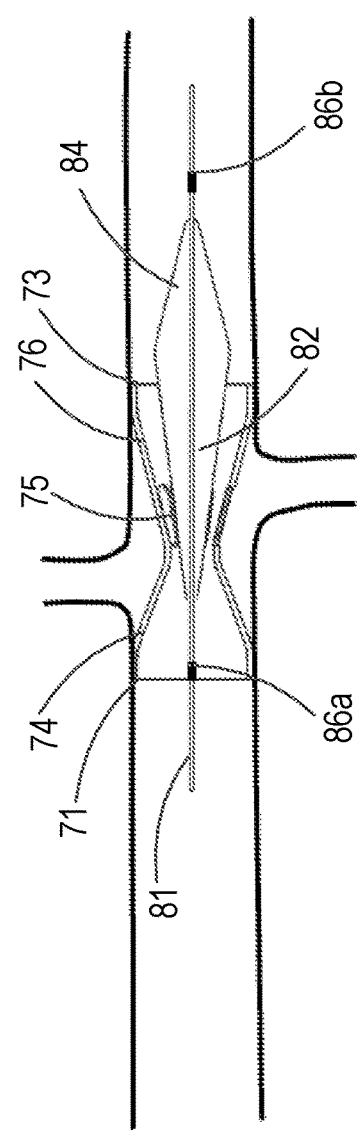
Figure 8C:
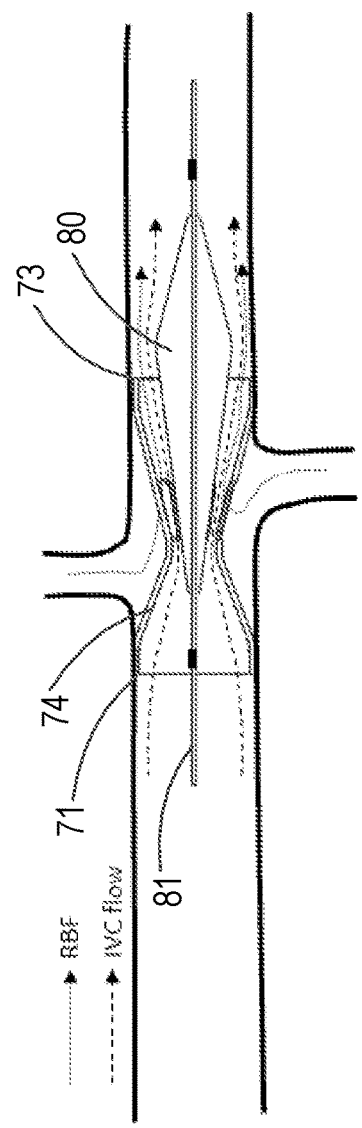

FIGS. 8A-8C illustrate flow modulator 70 positioned within a branched body lumen, e.g., the IVC. For example, stent 72 may be positioned such that upstream component 74 is in the IVC such that inlet 71 is upstream from a branch off to the left and right renal veins and downstream component 76 is in the IVC such that exit 73 is downstream from the branch off to the renal veins. While the right and left renal veins are usually at different heights along the inferior vena cava, openings 75 are generally positioned in the vicinity of the branches to the renal veins (or other branch lumens when used for other indications). As shown in FIGS. 8A-8C, catheter 81 may include two pressure transducers 86a, 86b, which may be local diaphragm-based sensors, connected via the multi-lumen catheter to sensors at the proximal end of the device, or optical pressure sensor. Upstream pressure transducer 86a may be coupled to catheter 81 upstream of core 80, and downstream pressure transducer 86b may be coupled to catheter 81 downstream of core 80, thereby providing information indicative of pressure differential across flow modulator 70. Alternatively, a single differential pressure transducer may be used that provides a reading of the pressure differential across the two sensor sites. The relative position of core 80 within stent 72 may be adjusted to tailor the performance of the flow characteristics within the vessel, based upon feedback from pressure transducers 86a, 86b, X-ray angiography, or other readings.

As shown in FIG. 8A, core 80 may initially be positioned within downstream component 76. As shown in FIG. 8B, core 80 may be moved proximally relative to stent 82 to effectively narrow the diffuser formed by the inner surface of stent 72 and the outer surface of core 80. As described above, the relative position of core 80 with respect to stent 72 may be determined based on feedback received via pressure transducers 86a, 86b. As shown in FIG. 8B, at least a portion of upstream region 82 of core 80 may be positioned within upstream component 74 of stent 72, thereby reducing the cross-sectional area of the nozzle of upstream component 74.

FIG. 8C illustrates IVC and RBF flow across flow modulator 70. For example, IVC blood only enters flow modulator 70 at inlet 71, and accelerates through the nozzle of upstream component 74 and around downstream region 82 of core 80 within the diffuser of downstream component 76, thereby creating reduced pressure at the entrainment region and increasing blood flow velocity to openings 75. In this manner, the invention may draw blood from the kidneys to the renal veins and then to the inferior vena cava, thereby improving kidney functionality, reducing necrotic damage to the kidneys, and/or treating heart failure.

Figure 9:
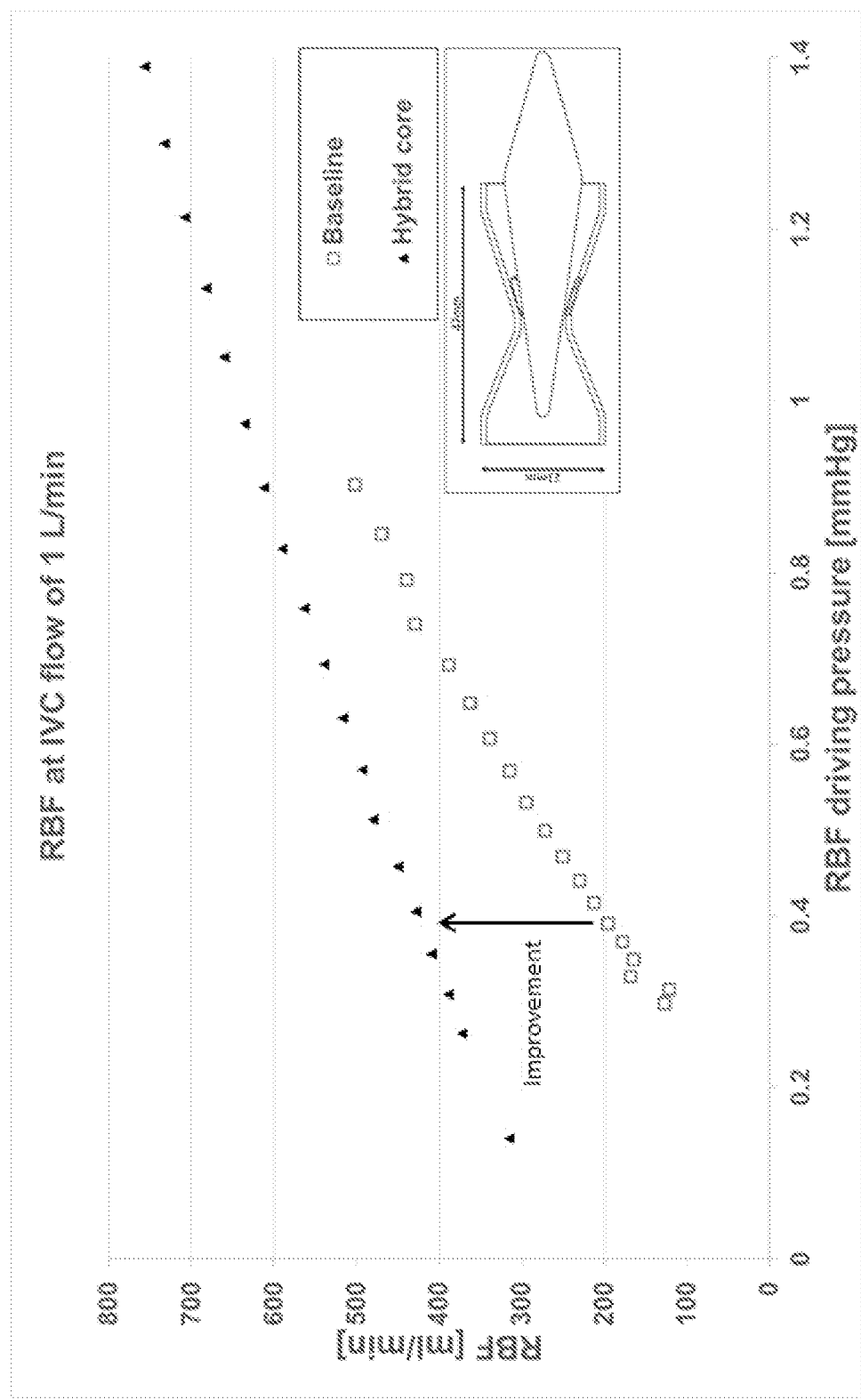
FIG. 9 is a graph of in-vitro results of improvements in simulated RBF using the fluid flow modulator of FIG. 7.

Referring now to FIG. 9, a graph of in-vitro results of improvements in simulated RBF using flow modulator 70 of the present invention is provided. In this experiment, flow modulator 70 was placed within a mock silicone IVC model that included renal veins. The IVC flow was set to varying flow rate levels. For the results shown in FIG. 9, the working fluid was water at room temperature, an IVC flow rate was set to 1 L/min, and right atrial pressure was set to 8 mmHg. The flow rate exiting the renal veins was measured over a varying range of driving pressures. FIG. 9 shows RBF measured with a flow modulator placed in the mock IVC, compared to a similar experiment without a flow modulator. The comparison of RBF between Baseline (without device) and the core element was evaluated for a given RBF driving pressure. For example, for RBF driving pressure of 0.4 mmHg the baseline BF was about 200 ml/min. When the device was added to the IVC model the RBF increased to about 420 ml/min.

Figure 10A:
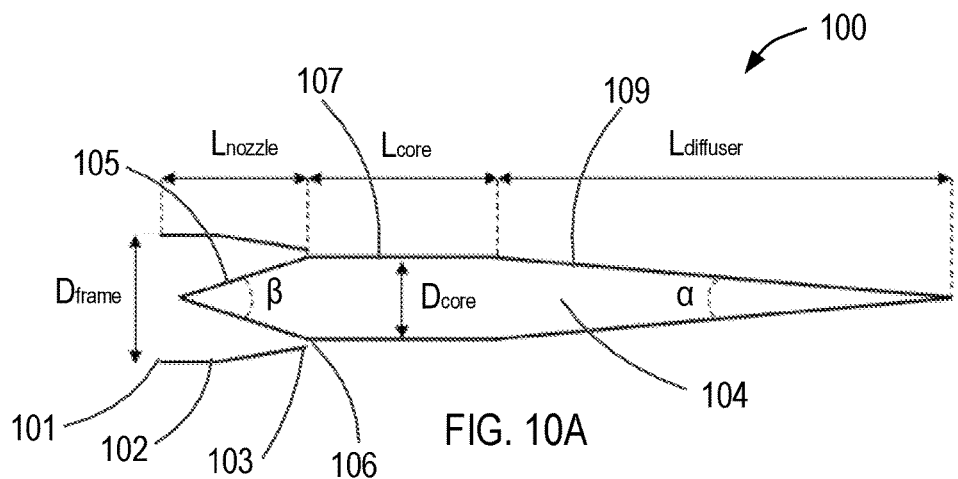
FIG. 10A is a schematic view of another exemplary fluid flow modulator constructed in accordance with the principles of the present invention.
Figure 10B:
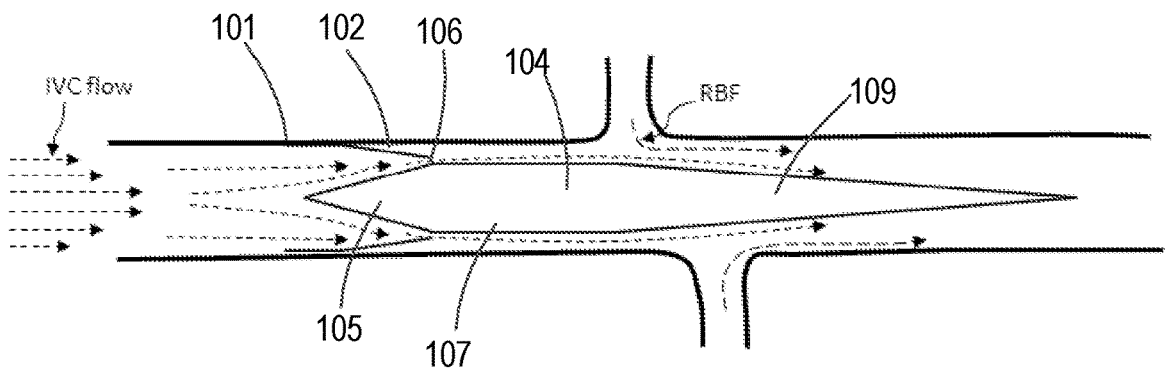
FIG. 10B is a schematic view of the fluid flow modulator of FIG. 10A positioned within a body lumen in accordance with the principles of the present invention.
Figure 10C:
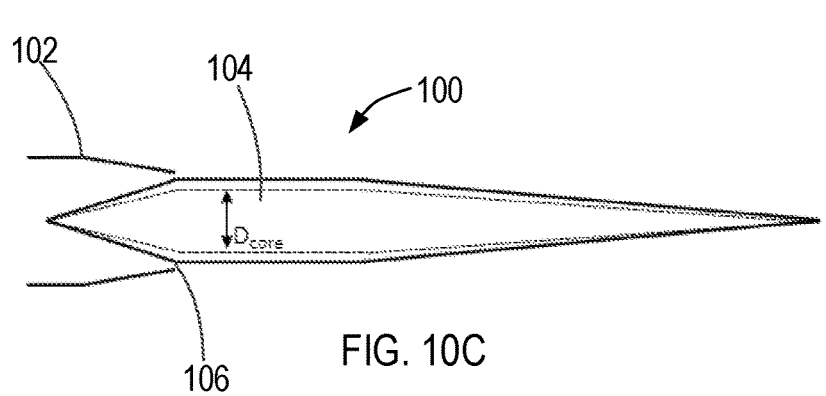
FIG. 10C illustrates the inflation of the core of the fluid flow modulator of FIG. 10A in accordance with the principles of the present invention.

Referring now to FIGS. 10A to 10C, another exemplary fluid flow modulator constructed in accordance with the principles of the present invention is provided. Flow modulator 100 may include stent 102 and expandable core 104 disposed within the passageway of stent 102. Stent 102 may be formed from a single frame that is fully coated or at least partially coated with a biocompatible material in accordance with the principles of the present invention. For example, as shown in FIG. 10A, stent 102 is a fully coated stent having inlet 101 at an upstream end of stent 102 and outlet 103 at a downstream end of stent 102. The cross-sectional area of stent 102 may decrease in the direction from inlet 101 to outlet 103. As shown in FIG. 10A, at least a portion of stent 102 in the vicinity of inlet 101 may have a constant diameter before the cross-sectional area of stent 102 begins to decrease towards outlet 102. Moreover, stent 102 may have a fixation area, e.g., the constant diameter portion of stent 102, which may contact the inner wall of the blood vessel to maintain stent 102 in the desired position within the blood vessel. $D_{frame}$ is the diameter at the largest diameter section of stent 102. $L_{nozzle}$ is the length of the nozzle portion formed by the convergence of stent 102 from inlet 101 to outlet 103 and the upstream diverging region of core 104 as described in further detail below.

Core 104 may include upstream diverging region 105, core region 107, and downstream converging region 109. Upstream diverging region 105 has a first end, e.g., the most upstream point of core 104, and a cross-sectional area that increases from the first end towards core region 107 such that upstream diverging region 105 of core 104 diverges along the direction of IVC flow. Core region 107 may have a constant diameter along its axial length, e.g., $D_{core}$, and extend from upstream diverging region 105 to downstream converging region 109. Downstream converging region 109 has a second end, e.g., the most downstream point of core 104, and a cross-sectional area that decreases from core region 107 toward the second end such that downstream converging region 109 of core 104 converges along the direction of IVC flow. The cross-sectional area of upstream diverging region 105 may increase at a greater rate than the rate of decrease of the cross-sectional area of downstream converging region 109. For example, angle of divergence β of upstream diverging region 105 may be larger than angle of convergence α of downstream converging region 109. Moreover, core 104 may have a minimum overall length of, e.g., 5 cm. For example, $L_{core}$, the length of core region 107, may be up to 15 mm, and $L_{diffuser}$, the length of downstream converging region 109, may be up to 15 cm. In addition, core 104 may be symmetric about a longitudinal plane extending along the longitudinal axis of core 104.

Figure 10D:
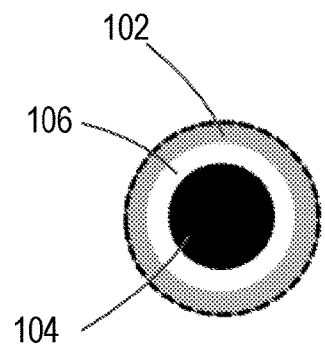
FIG. 10D is a cross-sectional view of the fluid flow modulator of FIG. 10A.

As shown in FIG. 10A, core 104 may be positioned within stent 102 to manipulate the effective angle of the nozzle to achieve the desired flow through flow modulator 70, thus enhancing the IVC blood flow and RBF. Specifically, the outer surface of core 104 and outlet 103 of stent 102 form circumferential slit 106, such that fluid flowing through inlet 101 of stent 102 will be accelerated through stent 102 and around upstream diverging region 105 of core 104, and exit through circumferential slit 106 into the blood vessel. As shown in FIG. 10A, circumferential slit 106 may be formed by outlet 103 of stent 102, and a portion of the outer surface of core 104 where upstream diverging region 105 joins with core region 107. FIG. 10D is a cross-sectional view of flow modulator 100 illustrating circumferential slit 106 formed by stent 102 and core 104. In accordance with one aspect of the present invention, core 104 may be coupled to a catheter 81 for manipulator by a physician. Additionally or alternatively, core 104 may be coupled to stent 102 at outlet 103, e.g., an uncoated portion of stent 102 defining circumferential slit 106. Accordingly, at least a portion of stent 102, e.g., the uncoated portion downstream of outlet 103, may be flexible such that expansion of core 104 while outlet 103 of stent 102 maintains its cross-sectional area causes a decrease in the flow area of circumferential slit 106.

Referring now to FIG. 10B, flow modulator 100 is shown implanted within the IVC adjacent branched renal veins. As shown in FIG. 10B, IVC blood flows into inlet 101 of stent 102 and around upstream diverging region 105 through circumferential slit 106 and along core region 107, thereby creating a low pressure region in the vicinity of downstream converging region 109 causing entrainment of additional RBF into the fluid stream. The IVC blood flow and the additional RBF then flows through the diffuser portion of flow modulator 100 between downstream converging region 109 and the vessel wall.

As shown in FIG. 10C, core 104 may be a compliant, expandable body, e.g., an inflatable balloon. Accordingly, the cross-sectional area of core 104 may be adjusted via inflation of core 104. For example, core 104 may be fluidly coupled to an inflation/deflation source, e.g., via a catheter having an inflation/deflation lumen, for inflating/deflating core 104. Accordingly, core 104 may be selectively inflated/deflated via inflation/deflation lumen(s) to achieve the desired IVC resistance. Specifically, as $D_{core}$ increases, the flow area of circumferential slit 106 decreases, and as $D_{core}$ decrease, the flow area of circumferential slit 106 increases. As described above, pressure transducers, e.g., an upstream pressure transducer and a downstream pressure transducer, may provide feedback regarding pressure differential across flow modulator 100, such that a physician may selectively inflate/deflate core 104 to achieve a desired size of circumferential slit 106, and accordingly, a desired blood flow across flow modulator 100.

Figure 11A:
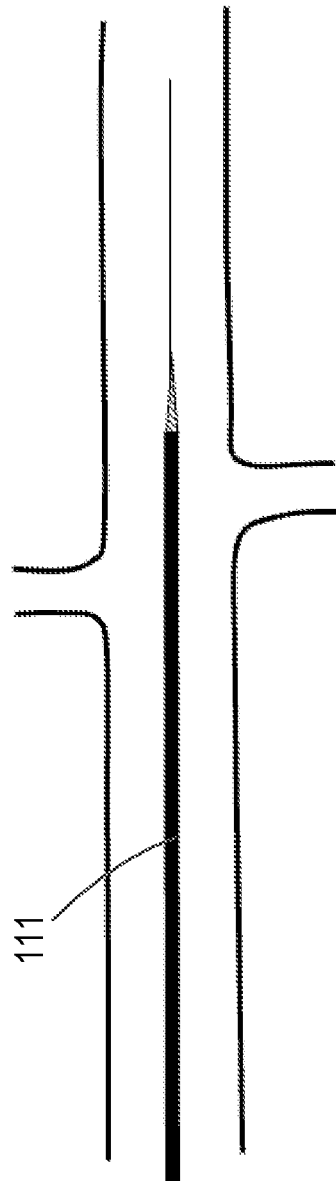
FIGS. 11A-11C schematically illustrate the delivery of another exemplary fluid flow modulator within a body lumen in accordance with the principles of the present invention.
Figure 11B:
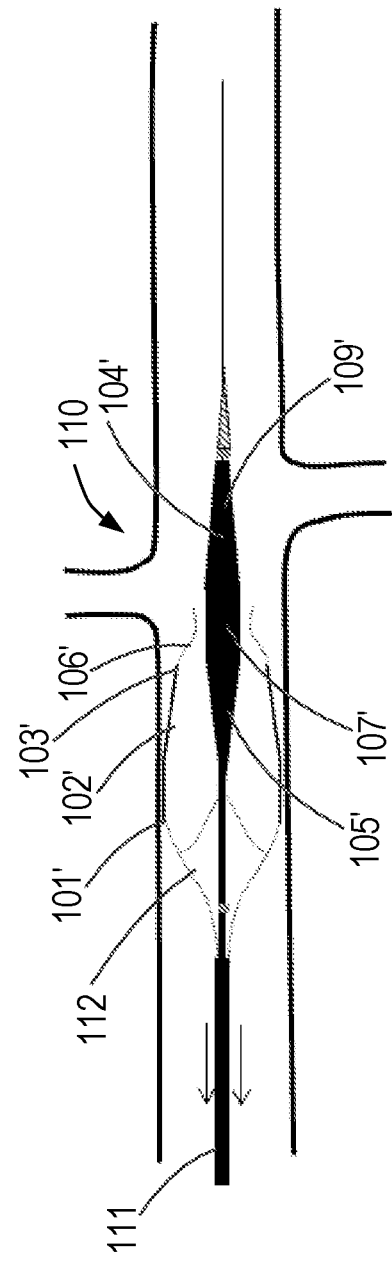
Figure 11C:
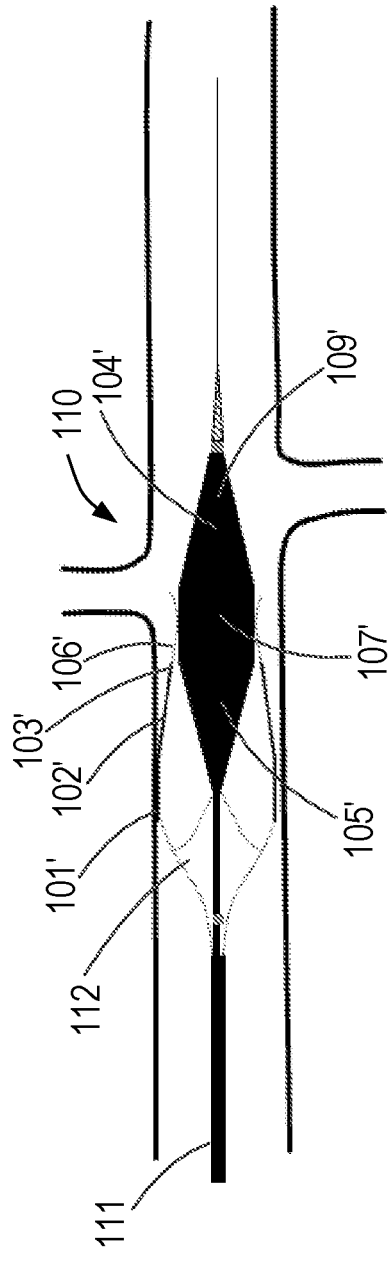

FIGS. 11A-11C schematically illustrate the delivery of another exemplary fluid flow modulator within a body lumen in accordance with the principles of the present invention for acute treatment. Flow modulator 110 may be constructed similar to flow modulator 70 of FIG. 7, with similar components having like-prime reference numerals. For example, stent 102' having inlet 101' and outlet 103' corresponds with stent 102 having inlet 101 and outlet 103, expandable core 110' having upstream diverging region 105', core region 107', and downstream converging region 109' corresponds with expandable core 110 having upstream diverging region 105, core region 107, and downstream converging region 109, and circumferential slit 106' corresponds with circumferential slit 106. As shown in FIG. 10B, stent 102' may be formed of a partially coated frame, such that stent 102 is coated between inlet 101' and outlet 103' to form the nozzle, but uncoated upstream of inlet 103 to define inlet 103 and uncoated downstream of outlet 103' to define circumferential slit 106'.

Referring again to FIG. 11A, delivery device 111 may be introduced to the target branched blood vessel, e.g., the IVC in the vicinity of the renal veins, to deliver flow modulator 110. Delivery device 111 may include, e.g., a delivery sheath and an inner assembly slidably disposed therein, the inner assembly coupled to flow modulator 110 in its collapsed, delivery state within the delivery sheath. As shown in FIG. 11B, the sheath may be retracted while the inner assembly and flow modulator 110 remain in place to expose flow modulator 110 out the distal end of the delivery sheath, thereby permitting flow modulator 110 to self-expand from its collapsed, delivery state, to its expanded, deployed state. As shown in FIG. 11B, a proximal portion the frame of stent 102' may remain coupled to delivery device 111, and core 104' may be remain coupled to a catheter of delivery device 111, for an acute treatment.

As described above, pressure transducers, e.g., an upstream pressure transducer and a downstream pressure transducer, may provide feedback regarding pressure differential across flow modulator 110, such that a physician may selectively inflate/deflate core 104' to achieve a desired size of circumferential slit 106', and accordingly, a desired blood flow across flow modulator 110. For example, FIG. 11C illustrates flow modulator 110 when core 104' has been selectively expanded when compared with FIG. 11B. As shown in FIG. 11C, circumferential slit 106' has a smaller flow area than circumferential slit 106' of FIG. 11B. Accordingly, IVC blood will flow into inlet 101' of stent 102' and around upstream diverging region 105' through circumferential slit 106' and along core region 107', thereby creating a low pressure region in the vicinity of downstream converging region 109' causing entrainment of additional RBF into the fluid stream. The IVC blood flow and the additional RBF will then flow through the diffuser portion of flow modulator 110 between downstream converging region 109' and the vessel wall.

Figure 12:
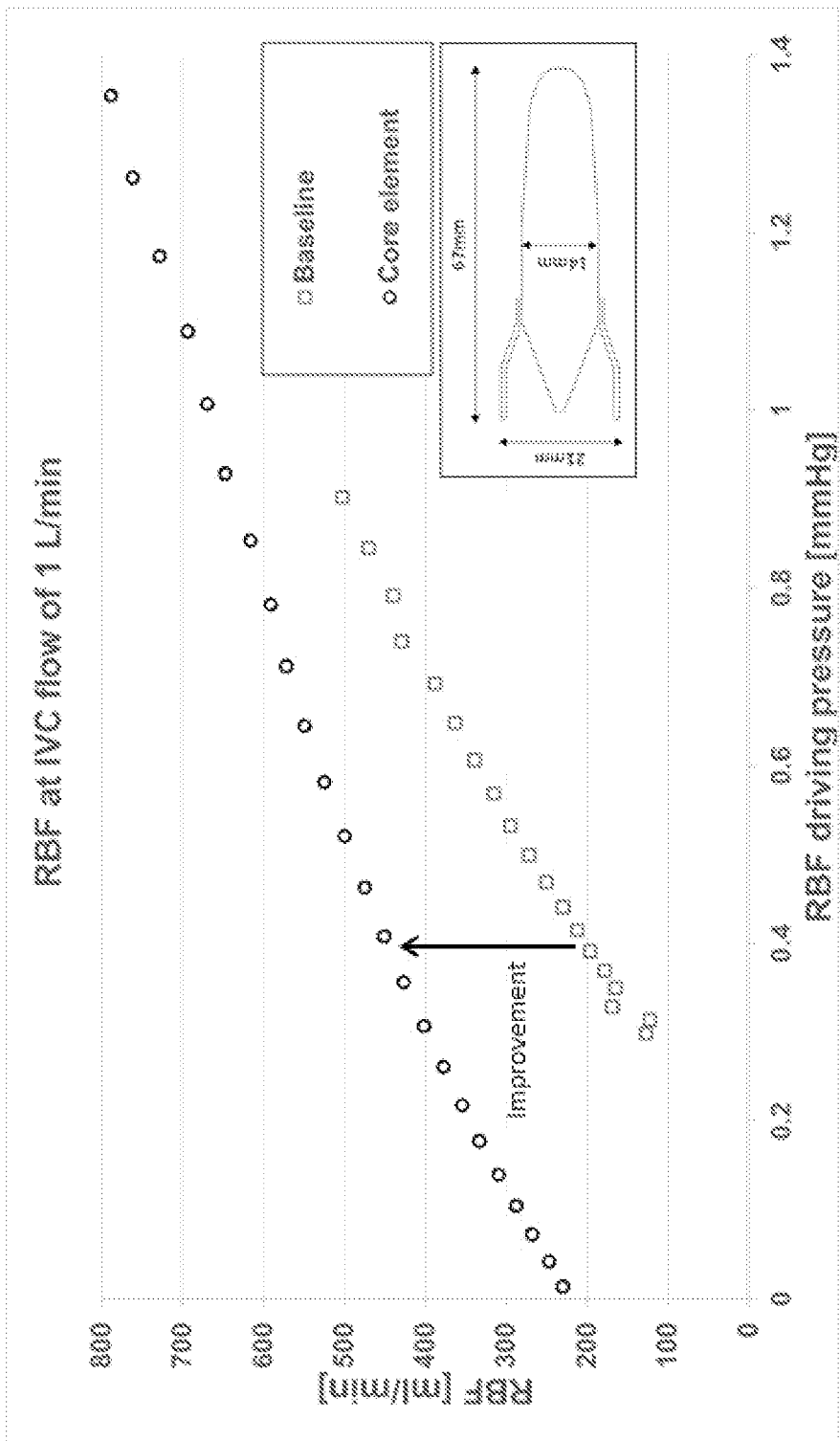
FIG. 12 is a graph of in-vitro results of improvements in simulated RBF using the fluid flow modulator of FIG. 10A.

Referring now to FIG. 12, a graph of in-vitro results of improvements in simulated RBF using a flow modulator constructed similar to flow modulator 100 and flow modulator 110 of the present invention is provided. In this experiment, the flow modulator was placed within a mock silicone IVC model that included renal veins. The IVC flow was set to varying flow rate levels. For the results shown in FIG. 12, the working fluid was water at room temperature, an IVC flow rate was set to 1 L/min, and right atrial pressure was set to 8 mmHg. The flow rate exiting the renal veins was measured over a varying range of driving pressures. FIG. 9 shows RBF measured with a flow modulator placed in the mock IVC, compared to a similar experiment without a flow modulator. The comparison of RBF between Baseline (without device) and the core element was evaluated for a given RBF driving pressure. For example, for RBF driving pressure of 0.4 mmHg the baseline BF was about 200 ml/min. When the device was added to the IVC model the RBF increased to about 440 ml/min.

Figure 13A:
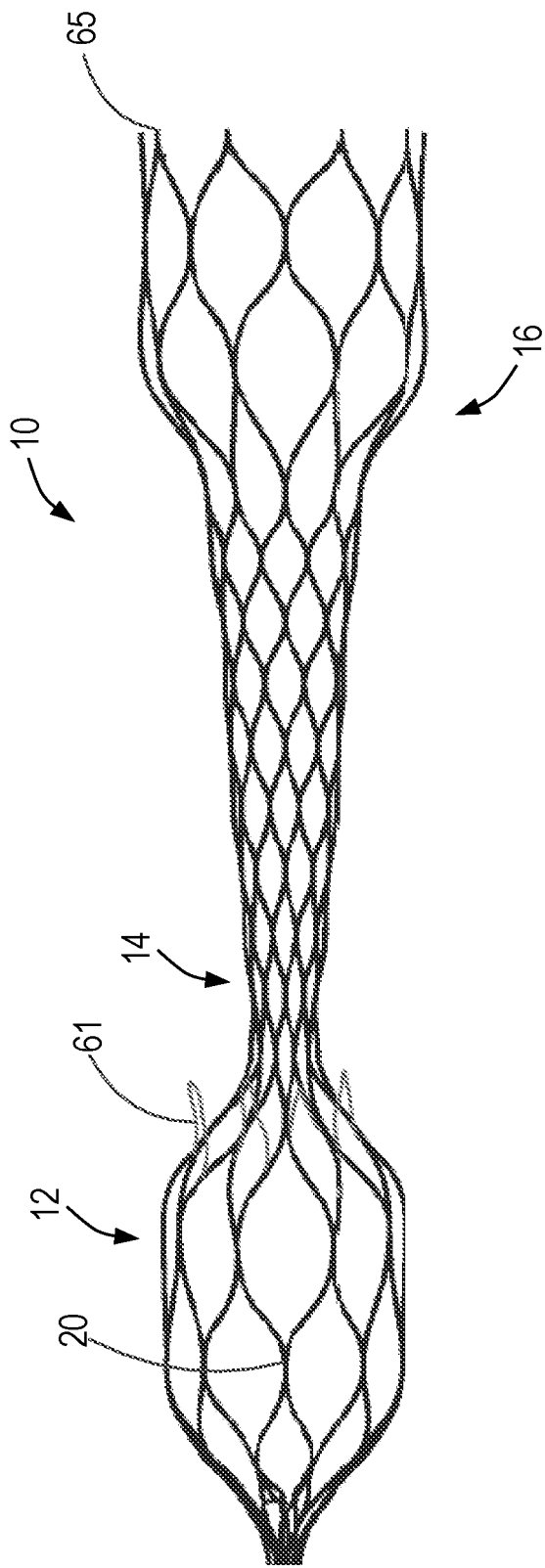
FIGS. 13A-13D illustrate various alternative fixation elements of the fluid flow modulator constructed in accordance with the principles of the present invention.

Referring now to FIGS. 13A-13D, flow modulator 10 may include one or more various types of fixation elements for securing flow modulator 10 within a vessel, and thereby prevent migration of flow modulator 10 within the vessel. For example, as shown in FIG. 13A, upstream component 12 of flow modulator 10 may include a plurality of anchors 61 extending away from the external surface of frame 20. Anchors 61 may be disposed circumferentially along the outer surface of flow modulator 10. Additionally, or alternatively, plurality of anchors 61 may be disposed on downstream component 16, to engage with the vessel. In addition, as shown in FIG. 13A, the distal ends of downstream component 16 may include additional fixation elements, e.g., barbs 65, that may penetrate the tissue to thereby prevent migration of flow modulator 10 within the vessel. For example, barbs 65 may be curved radially outward from the longitudinal axis of flow modulator 10.

Figure 13D:
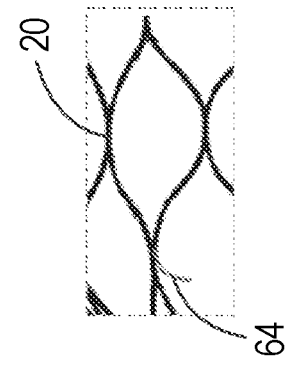
Figure 13C:
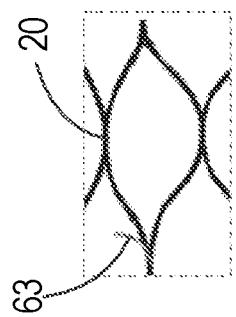
Figure 13B:
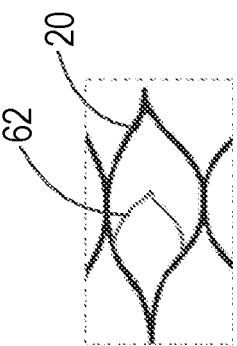

As shown in FIG. 13B, the plurality of anchors extending from frame 20 may include anchors 62 with two ends coupled to frame 20, thereby forming a flap-like anchor. As shown in FIG. 13C, the plurality of anchors extending from frame 20 may include anchors 63, which extends upward from frame 20. As shown in FIG. 13D, the plurality of anchors extending from frame 20 may include anchors 64, which extends downward from frame 20. Anchors 61, 62, 63, 64 may engage with the vessel to thereby prevent migration of flow modulator 10. In some embodiments, anchors 61, 62, 63, 64 may penetrate the tissue to secure flow modulator 10 within the vessel.

Moreover, the flow modulators described herein may be used in conjunction with an external pump and a control system as described in WO 2020/109979, the entire contents of which are incorporated herein by reference. For example, the external pump may be an intermittent pneumatic compression (IPC) or a cardiac enhanced external counterpulsation (EECP) pump (such as the ArtAssist® device, available by ACI Medical, San Marcos, Calif.). The pump may be programmed to mimic the natural pumping action of an ambulatory calf and/or foot to move blood in the deep veins of the leg, thereby reducing deep vein thrombosis formation. In addition, the pump may provide power to the flow modulator. The external pump and the control system may be fully mobile and/or battery operated. For example, the external pump and the control system be worn by the patient, e.g., around the patient's leg.

While preferred illustrative embodiments of the invention are described above, it will be apparent to one skilled in the art that various changes and modifications may be made therein without departing from the invention. For example, the flow modulators described herein may be installed in the inferior vena cava at the branch to a hepatic vein. Accordingly, additional blood may be entrained from the hepatic veins into the IVC, thereby improving splanchnic circulation. Acutely or chronically implanting a flow modulator in the IVC adjacent the hepatic veins may improve liver function and/or may be used instead of, or in parallel to, a TIPS procedure. Advantageously, the flow modulator improves hepatic flow to the inferior vena cava allowing blood to enter the liver for natural filtering (in contrast to a TIPS procedure that bypasses blood from the liver). The flow modulator, whether used together with a TIPS procedure or in place of a TIPS procedure, is expected to treat conditions such as portal hypertension (often due to liver cirrhosis) which frequently leads to intestinal bleeding, life-threatening esophageal bleeding (esophageal varices), the buildup of fluid within the abdomen (ascites), and/or hepatorenal syndrome.

Additionally or alternatively, the flow modulators described herein may be installed in the inferior vena cava to entrain additional blood from both the renal and hepatic veins. For example, the exit of the downstream component may be downstream to the hepatic vein while the inlet of the upstream component is upstream to the renal veins. In one study, the mean distance from a downstream renal vein to the hepatic vein was 6 cm, and the mean distance from the upstream-most renal vein to the downstream-most renal vein was 2.5 cm, and thus a flow modulator having an overall distance of 8.5 cm between the fixation areas of upstream component 12 and downstream component 16 may be anchored within the IVC to improve both renal and hepatic perfusion simultaneously.

Moreover, the flow modulators described herein may be installed in an aneurysm to lower pressure at the aneurysm site, and reduce the risk that the aneurysm will increase in size or burst, and may even cause the aneurysm to decrease in size. In this case, the flow modulator is expected to provide beneficial effect even without sealing against the aneurysm. In addition, if there are one or more side branch lumens at or near the aneurysm site, the device not only will reduce the pressure but also permit blood to flow to the side branches. In this application, the device of the present invention provides significant benefit as compared to previously-known circular stent grafts, which disadvantageously may block the side branches. If there are no side branches, then the device is expected to reduce pressure without increasing the blood flow. Optionally, a filter may be used with the flow modulator to prevent embolic debris from flowing from the aneurysm to other blood vessels.

Any of the foregoing embodiments of the device of the present invention may serve to divert emboli or other debris, so there is no need to use an extra filtration device. One example is using the upstream component or downstream component at or near the carotid arteries to divert emboli or other debris.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A flow modulator device for altering fluid flow through a body lumen, the body lumen coupled to a branch lumen, the flow modulator device comprising:
    an upstream component configured to transition between a collapsed delivery state and an expanded deployed state, the upstream component having an inlet, an outlet, and a cross-sectional flow area that converges from the inlet towards the outlet in the expanded deployed state, the upstream component comprising a retrieval portion configured to facilitate retrieval of the flow modulator device, the retrieval portion comprising a constricted section at an upstream end of the flow modulator device, the retrieval portion converging from the inlet towards the upstream end in the expanded deployed state, the retrieval portion comprising a hook at the constricted section at the upstream end of the flow modulator device such that the hook is configured to be pulled to collapse the upstream component;
    a downstream component configured to transition between a collapsed delivery state and an expanded deployed state, the downstream component having an entry, an exit, and a cross-sectional flow area that diverges from the entry towards the exit in the expanded deployed state, the downstream component comprising a plurality of anchors radially spaced around a downstream end of the downstream component, the plurality of anchors configured to be coupled to a delivery device to maintain the downstream component in the collapsed delivery state upon exposure to the body lumen from a sheath of the delivery device; and
    an entrainment region between the inlet of the upstream component and the exit of the downstream component, the entrainment region comprising one or more openings,
    wherein the flow modulator device is configured to be positioned within the body lumen to accelerate a fluid stream passing through the upstream component towards the downstream component to generate a low pressure region in the vicinity of the entrainment region that entrains additional fluid into the fluid stream via the one or more openings as the fluid stream passes into the downstream component.

2. The flow modulator device of claim 1, wherein the upstream component and the downstream component are formed from a single frame defining a plurality of cells.

3. The flow modulator device of claim 1, wherein the upstream component and the downstream component are at least partially coated with a biocompatible material, thereby exposing the one or more openings and defining the inlet.

4. The flow modulator device of claim 1, wherein the retrieval portion comprises one or more eyelets at the upstream end that meet together at the hook.

5. The flow modulator device of claim 1, wherein the retrieval portion is configured to be coupled to a retrieval device to permit retrieval of the flow modulator device.

6. The flow modulator device of claim 5, wherein the retrieval portion is configured to remain coupled to the retrieval device for an acute treatment.

7. The flow modulator device of claim 1, wherein the retrieval portion comprises an uncoated portion of a frame forming the flow modulator device.

8. The flow modulator device of claim 1, wherein the plurality of anchors are configured to be disengaged from the delivery device to transition the downstream component from the collapsed delivery state and the expanded deployed state.

9. The flow modulator device of claim 1, wherein the one or more openings comprises a plurality of openings radially spaced around the entrainment region.

10. The flow modulator device of claim 9, wherein the plurality of openings are longitudinally extending slots in the flow modulator device.

11. The flow modulator device of claim 1, wherein the downstream component comprises a first diverging portion and a second diverging portion downstream from the first diverging portion, wherein an average angle of divergence of the second diverging portion is greater than an average angle of divergence of the first diverging portion.

12. The flow modulator device of claim 1, wherein the upstream component comprises a nozzle that accelerates the fluid stream passing through the upstream component and the downstream component comprises a diffuser that decelerates the fluid stream having the entrained additional fluid passing through the downstream component.

13. The flow modulator device of claim 1, wherein the entrainment region is integrally formed with the downstream component.

14. A system comprising the flow modulator device and the delivery device of claim 1, the delivery device comprising:
    the sheath having a lumen sized to hold the flow modulator device therewithin such that the upstream and downstream components are in the collapsed delivery state during delivery; and
    an inner assembly slidably disposed within the lumen of the sheath to facilitate deployment of the flow modulator device out a distal end of the sheath, the inner assembly comprising an end cap configured to be removeably coupled to the distal end of the sheath during delivery.

15. The system of claim 14, wherein the end cap comprises a mount having a plurality of receptacles configured to be releasably engaged with the plurality of anchors of the downstream component, and an outer cover slidably disposed over the plurality of receptacles of the mount, such that, when the outer cover is disposed over the plurality of receptacles and the plurality of anchors, the downstream component of the flow modulator device remains in the collapsed delivery state, and when the outer cover is not disposed over the plurality of receptacles, the plurality of anchors disengages with the plurality of receptacles and the downstream component transitions from the collapsed delivery state to the expanded deployed state.

16. The system of claim 15, wherein the sheath is configured to be retracted proximally relative to the inner assembly and the flow modulator device in the collapsed delivery state, to expose the flow modulator device out the distal end of the sheath while the plurality of anchors is engaged with the plurality of receptacles such that the downstream component of the flow modulator device remains in the collapsed delivery state and while the retrieval portion of the upstream component remains coupled to the delivery device.

17. The system of claim 16, wherein the delivery device and the flow modulator device are configured to be repositioned within the body lumen while the flow modulator device is exposed out the distal end of the sheath and in the collapsed delivery state.

18. The system of claim 14, wherein the delivery device further comprises a retrieval device, the retrieval device configured to be coupled to the retrieval portion of the upstream component of the flow modulator device during delivery.

19. The system of claim 18, wherein the retrieval device is configured to remain coupled to the retrieval portion of the upstream component during an acute treatment, or
wherein the retrieval device is configured to be decoupled from the retrieval portion of the upstream component to chronically implant the flow modulator device.

20. The system of claim 18, wherein the sheath is configured to be moved distally relative to the retrieval device while the retrieval device is coupled to the retrieval portion of the upstream component to transition the flow modulator device from the expanded deployed state to the collapsed delivery state within the lumen of the sheath.

21. The system of claim 14, wherein the inner assembly comprises an adaptive pattern corresponding to a volume curve of the upstream component and the downstream component in the collapsed delivery state within the sheath, the adaptive pattern configured to support the flow modulator device in the collapsed delivery state within the sheath to prevent kinking in low volume regions.

22. A flow modulator device for altering fluid flow through a body lumen, the body lumen coupled to a branch lumen, the flow modulator device comprising:
an upstream component configured to transition between a collapsed delivery state and an expanded deployed state, the upstream component having an inlet, an outlet, and a cross-sectional flow area that converges from the inlet towards the outlet in the expanded deployed state, the upstream component comprising a retrieval portion configured to facilitate retrieval of the flow modulator device;
a downstream component configured to transition between a collapsed delivery state and an expanded deployed state, the downstream component having an entry, an exit, and a cross-sectional flow area that diverges from the entry towards the exit in the expanded deployed state, the downstream component comprising a plurality of anchors radially spaced around a downstream end of the downstream component, the plurality of anchors configured to be coupled to a delivery device to maintain the downstream component in the collapsed delivery state upon exposure to the body lumen from a sheath of the delivery device; and
an entrainment region between the inlet of the upstream component and the exit of the downstream component, the entrainment region comprising one or more openings,
wherein the flow modulator device is configured to be positioned within the body lumen to accelerate a fluid stream passing through the upstream component towards the downstream component to generate a low pressure region in the vicinity of the entrainment region that entrains additional fluid into the fluid stream via the one or more openings as the fluid stream passes into the downstream component; and
an expandable core configured to be positioned within the flow modulator device.

23. A method for altering fluid flow through a body lumen, the body lumen coupled to a branch lumen, the method comprising:
positioning a delivery device within the body lumen, the delivery device comprising a sheath having a flow modulator device disposed therein in a collapsed delivery state, and an inner assembly slidably disposed within a lumen of the sheath, the inner assembly having an end cap coupled to a downstream component of the flow modulator device;
retracting the sheath relative to the inner assembly and the flow modulator device to expose the flow modulator device out a distal end of the sheath in the collapsed delivery state while an upstream component remains coupled to the delivery device;
disengaging the end cap from the downstream component of the flow modulator device to transition the flow modulator device from the collapsed delivery state to an expanded deployed state within the body lumen,
wherein a fluid stream passing through the upstream component of the flow modulator device towards the downstream component accelerates to generate a low pressure region in the vicinity of an entrainment region of the flow modulator device and to entrain additional fluid into the fluid stream as the fluid stream passes into the downstream component, and
pulling a hook of a retrieval portion of the flow modulator device to collapse the upstream component, the retrieval portion comprising a constricted section at an upstream end of the flow modulator device, the retrieval portion converging from an inlet of the upstream component towards the upstream end in the expanded deployed state, the hook being at the constricted section at the upstream end of the flow modulator device.

24. The method of claim 23, wherein, in the expanded deployed state within the body lumen, the upstream component is positioned in an inferior vena cava such that the inlet of the upstream component is upstream from a branch off to a renal vein and the downstream component is positioned in the inferior vena cava such that an exit of the downstream component is downstream from the branch off to the renal vein, thereby drawing blood from the renal vein and improving kidney functionality.

25. The method of claim 23, wherein, in the expanded deployed state within the body lumen, the upstream component is positioned in an inferior vena cava such that the inlet of the upstream component is upstream from a branch off to a hepatic vein and the downstream component is positioned in the inferior vena cava such that an exit of the downstream component is downstream from the branch off to the hepatic vein, thereby drawing blood to the inferior vena cava and improving splanchnic circulation.

26. The method of claim 23, further comprising:
moving the sheath distally relative to the flow modulator device to transition the flow modulator device from the expanded deployed state to the collapsed delivery state within the sheath;
and removing the delivery device and the flow modulator device from the body lumen.

27. The method of claim 23, further comprising:
decoupling the upstream component from the delivery device to chronically implant the flow modulator device within the body lumen; and
removing the delivery device from the body lumen.

28. The method of claim 23, further comprising repositioning the flow modulator device within the body lumen while the flow modulator device is exposed out the distal end of the sheath in the collapsed delivery state prior to disengaging the end cap from the downstream component of the flow modulator device.

\* \* \* \* \*